US012642432B2

(12) United States Patent
Thorn et al.

(10) Patent No.: US 12,642,432 B2
(45) Date of Patent: Jun. 2, 2026

(54) FIELD ADJUSTABLE OPTICS LENS

(71) Applicant: Phoenix-Micron, Inc., Bend, OR (US)

(72) Inventors: Jonathan Roy Thorn, Bend, OR (US);
Jonathan Scott Carr, Bend, OR (US)

(73) Assignee: Phoenix-Micron, Inc., Bend, OR (US)

( * ) Notice: Subject to any disclaimer, the term of this
patent is extended or adjusted under 35
U.S.C. 154(b) by 292 days.

(21) Appl. No.: 18/377,266

(22) Filed: Oct. 5, 2023

(65) Prior Publication Data

US 2024/0122476 A1     Apr. 18, 2024

Related U.S. Application Data

(60) Provisional application No. 63/416,330, filed on Oct.
14, 2022.

(51) Int. Cl.
| | |
|---|---|
| *A61B 3/15* | (2006.01) |
| *A61B 3/10* | (2006.01) |
| *A61B 3/16* | (2006.01) |
| *A61B 5/398* | (2021.01) |

(52) U.S. Cl.
CPC ............. *A61B 3/156* (2013.01); *A61B 3/102*
(2013.01); *A61B 3/16* (2013.01); *A61B 5/398*
(2021.01)

(58) Field of Classification Search
CPC ........... A61B 3/156; A61B 3/102; A61B 3/16;
A61B 5/398; A61B 5/6821
See application file for complete search history.

(56) References Cited

U.S. PATENT DOCUMENTS

| | | | | |
|---|---|---|---|---|
| 4,953,962 | A * | 9/1990 | Esswein ............. | G02B 27/0068 |
| | | | | 359/368 |
| 5,154,174 | A * | 10/1992 | Hawlina ................ | A61B 5/297 |
| | | | | 600/383 |
| 5,297,554 | A * | 3/1994 | Glynn .................. | A61B 5/6821 |
| | | | | 600/476 |
| 11,752,982 | B2 | 9/2023 | Chen et al. | |
| 2009/0211586 | A1 | 8/2009 | Shea et al. | |
| 2013/0120710 | A1* | 5/2013 | Buckland ........... | G01B 9/02057 |
| | | | | 351/206 |
| 2017/0363849 | A1 | 12/2017 | Doric et al. | |
| 2021/0219905 | A1* | 7/2021 | Hetling ................ | A61B 5/6821 |

(Continued)

FOREIGN PATENT DOCUMENTS

WO          2016205760 A1    12/2016

OTHER PUBLICATIONS

PCT/US2023/076065, "International Preliminary Report on Patent-
ability", Apr. 24, 2025, 8 pages.
(Continued)

*Primary Examiner* — Ephrem Z Mebrahtu
(74) *Attorney, Agent, or Firm* — Kilpatrick Townsend &
Stockton LLP

(57)          ABSTRACT

The present disclosure provides an apparatus including a
lens housing coupled to a lens assembly, a first lens disposed
in a first end of the lens housing, a lens holder disposed in
a second end of the lens housing, a lens aligner coupled to
the lens assembly, and an optical element. The optical
element is insertable laterally into the lens assembly to
adjust a transverse position of the first lens and the second
lens based on a thickness of the optical element to align a
first axis of the first lens and the second lens to a second axis
of a third lens positioned in the lens assembly for imaging
an eye.

14 Claims, 30 Drawing Sheets

(56) References Cited

U.S. PATENT DOCUMENTS

| | | |
|---|---|---|
| 2022/0304563 A1 | 9/2022 | Sachs et al. |
| 2024/0407886 A1 | 12/2024 | Thorn |
| 2025/0249492 A1 | 8/2025 | Sonzogni |

OTHER PUBLICATIONS

PCT/US2023/076065, "International Search Report and Written Opinion", Jan. 23, 2024, 11 pages.
U.S. Appl. No. 18/665,008, "Notice of Allowance", Nov. 7, 2025, 11 pages.

* cited by examiner

First lens glued and potted into the tip

206

204

Second lens

100

720

Electrically insulating
PTFE film

100

924

924

1026

1026

V-grooves in the lens aligners position the tip

922

1434

100

Two set screws
on each side

Third lens and holder

1636

Laser injector attachment

922

Dichroic filter holder

1638

Beam dump prevents light from reflecting off the backside of the dichroic and creating artifacts in the image The light shifts up about 1/3 the thickness of the dichroic

2140

1638

Dichroic would have to be swapped out
depending on application

2140

1638

A mirror image of the lens holder provides support on the other side

A screw in the dichroic holder clamps onto the lens

2542

100

Conductive tip can sense contact with the eye

Could be an EKG sensor

2542

3052

Attach a proper
connector to the tip

100

FIELD ADJUSTABLE OPTICS LENS

CROSS-REFERENCES TO RELATED APPLICATIONS

The present application claims the benefit of and priority to U.S. Provisional Application No. 63/416,330, filed Oct. 14, 2022, the entire contents of which is incorporated herein by reference for all intents and purposes.

BACKGROUND OF THE INVENTION

Eye-imaging devices are used to detect potential eye diseases, vision impairments, and indicators of various other diseases. The eye-imaging devices used may include multiple lenses and other optical elements.

Although eye-imaging devices have been developed, there is a need in the art for improved methods and systems related to eye-imaging devices.

SUMMARY OF THE INVENTION

The present disclosure relates to an apparatus, system, and method for providing a field adjustable optics lens for an imaging device. In particular, the present disclosure provides an apparatus, system, and method for providing an eye-imaging apparatus that automatically adjusts a positioning of lenses with respect to each other based on an optical element being used. Beneficially, the eye-imaging apparatus can reduce deconstruction, reconstruction, and manipulation of the components of the eye-imaging apparatus to reposition the lenses for a particular optical element.

Eye-imaging devices may use various imaging modalities, such as optical coherence tomography, laser injection, and electroretinogram techniques. It may be beneficial to be able to switch between multiple imaging modalities in a primary imaging path of an eye-imaging device during an imaging of an eye. However, the arrangement and positioning of the lenses and optical elements may depend on the imaging modality. Thus, embodiments of the present invention enable the use of multiple imaging modalities during imaging in a manner that an operator can accurately and efficiently set up by including field adjustable optics.

According to an embodiment of the present invention, an apparatus is provided. The apparatus includes a lens housing coupled to a lens assembly, a first lens disposed in a first end of the lens housing, a lens holder disposed in a second end of the lens housing, and a second lens disposed in the lens holder. The apparatus also includes a lens aligner coupled to the lens assembly and an optical element that is configured to be inserted laterally into the lens assembly to adjust a transverse position of the first lens and the second lens based on a thickness of the optical element to align a first axis of the first lens and the second lens to a second axis of a third lens positioned in the lens assembly for imaging an eye.

According to another embodiment of the present invention, a lens tip of an eye-imaging device is provided. The lens tip includes a lens housing comprising a first lens and a second lens aligned along an optical axis. The lens housing is coupled to a lens assembly and is configured to be positioned with respect to a thickness of an optical element in the lens assembly. The lens tip also includes a tip configured to contact an eye. The tip is electrically conductive.

Numerous benefits are achieved by way of the present disclosure over conventional techniques. For example, embodiments of the present disclosure provide an apparatus that can be attached to an imaging device that adjusts a position of a lens tip including two lenses with respect to a third lens based on a thickness of an optical element. As a result, the axes of the lenses can be aligned automatically during insertion of the optical element, without additional manipulation by an operator. The apparatus can also include a tip with a sensor for monitoring contact to an eye or a pressure of contact with an eye. These and other embodiments of the disclosure, along with many of their advantages and features, are described in more detail in conjunction with the text below and attached figures.

DETAILED DESCRIPTION OF SPECIFIC EMBODIMENTS

The present disclosure describes a number of embodiments related to an apparatus, system, and methods for providing a field adjustable optics lens for an eye-imaging camera. In some embodiments, the present disclosure provides an apparatus including a lens tip having a first lens and a second lens. The second lens can be positioned within a lens holder of the lens tip. The lens tip can attach to a lens assembly that includes an optical element (e.g., Lyot stop or dichroic beamsplitter) and a third lens. The optical element can be coupled to a lens aligner so that when the optical element is positioned within the lens assembly, the lens aligner can position the first lens and the second lens with respect to the third lens. For instance, the first lens and the second lens may need to be offset from the third lens at a distance of one-third of a thickness of the optical element if the optical element is a dichroic beamsplitter to align the first lens, the second lens, and the third lens for imaging of an eye. Therefore, inserting the dichroic beamsplitter into the lens assembly using the lens aligner with at least one groove (e.g., v-groove) can position the first lens and the second lens at the appropriate position.

The present disclosure also provides a tip of the lens that is capable of sensing properties associated with contacting the eye. For instance, the tip may include a pressure transducer for measuring the force of contact of the imaging device to the eye. Alternatively, the tip may include an electroretinogram (ERG) sensor, an electrocardiogram (EKG) sensor for measuring electrical signals of the eye, or any combination thereof. The tip may additionally include multiple conductive contacts (e.g., electrically conductive contacts) useful for determining whether the tip is in contact with a sufficient portion of the eye or whether an inadequate amount of gel or an air bubble is present between the tip and the eye.

Figure 1:
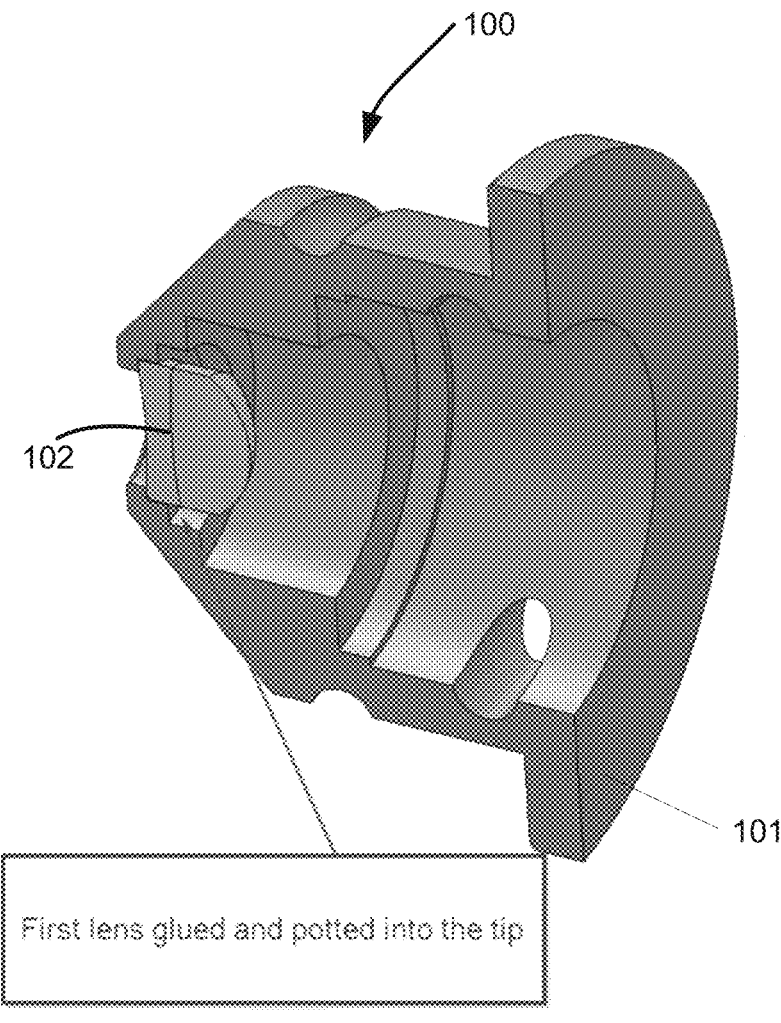
FIG. 1 illustrates a section view of components of a lens tip of an apparatus according to some embodiments.
Figure 2:
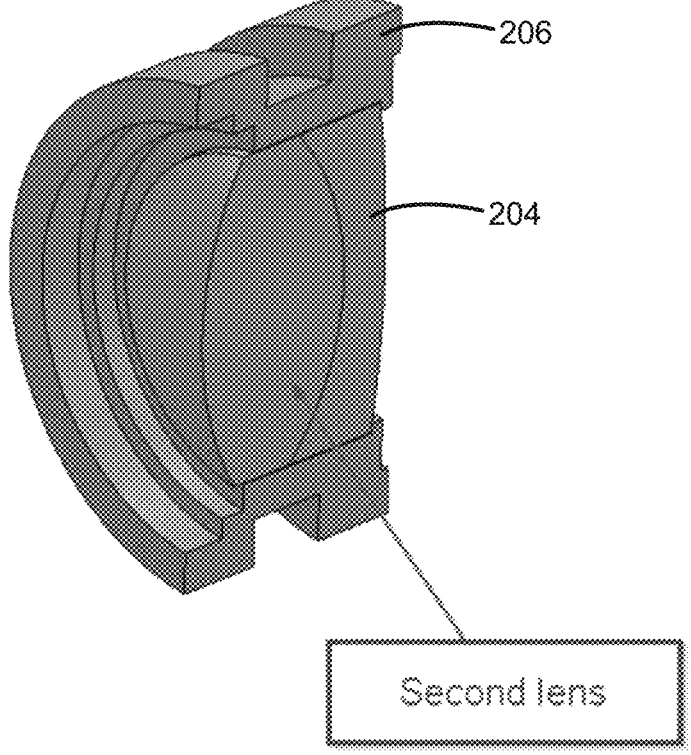
FIG. 2 illustrates another section view of components of a lens tip of an apparatus according to some embodiments.
Figure 3:
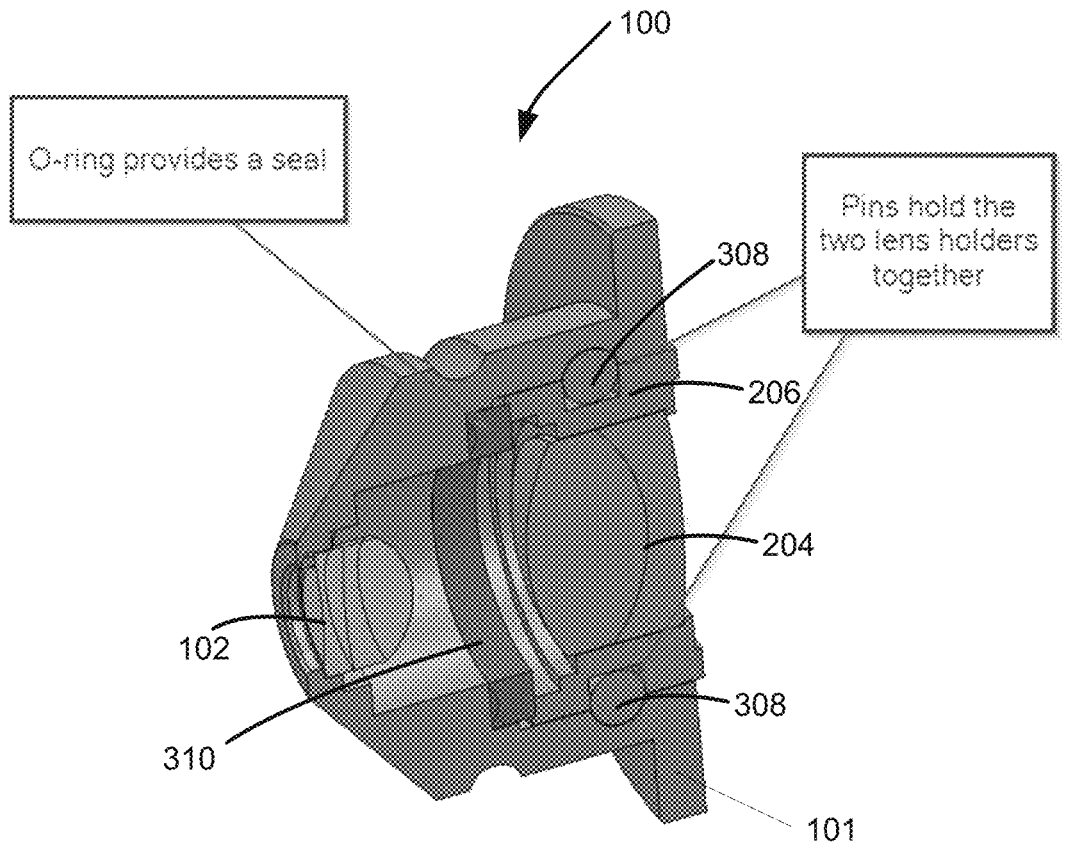
FIG. 3 illustrates another section view of components of a lens tip of an apparatus according to some embodiments.
Figure 4:
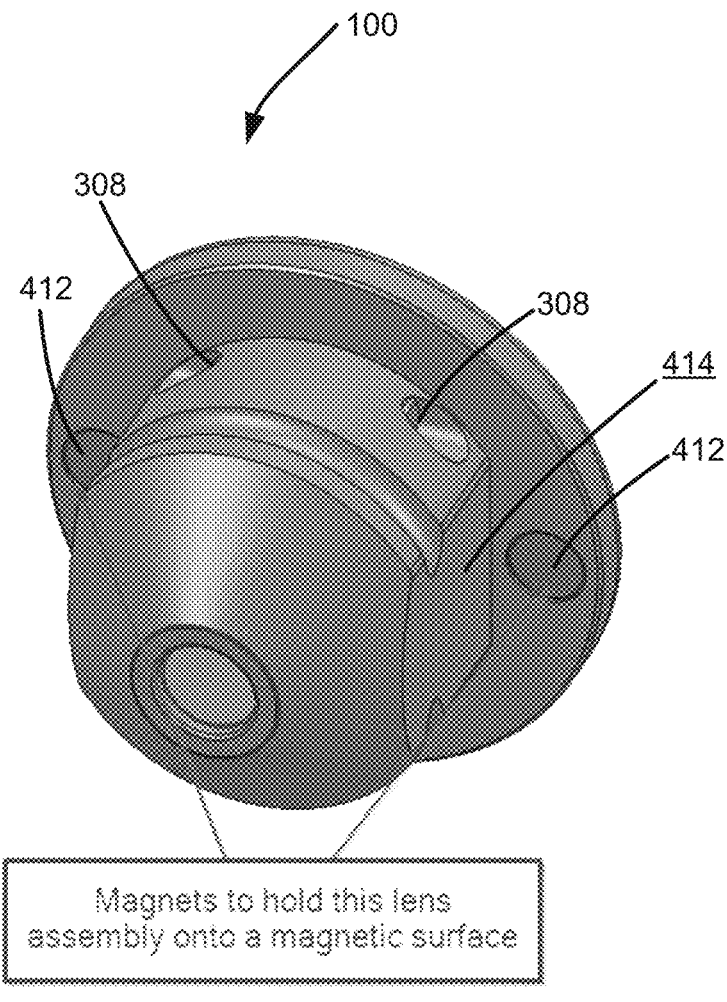
FIG. 4 illustrates another perspective view of a lens tip according to some embodiments.
Figure 5:
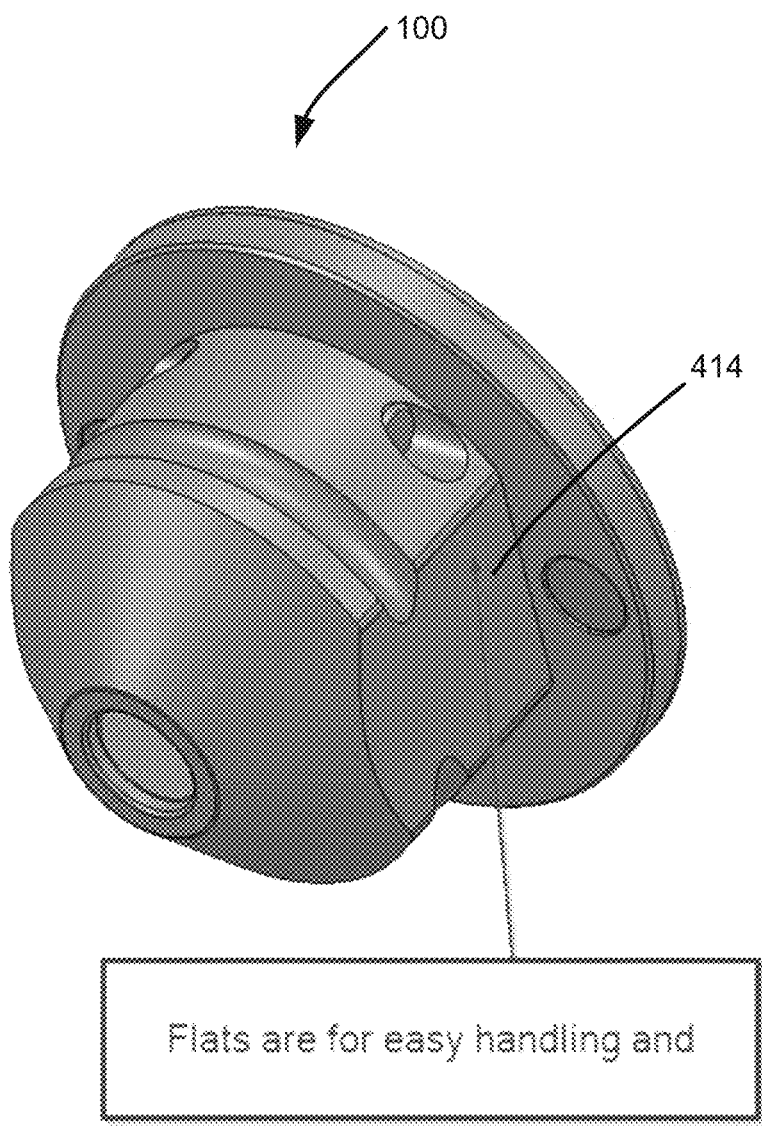
FIG. 5 illustrates another perspective view of a lens tip according to some embodiments.

FIGS. 1-3 illustrate section views of components of a lens tip 100 of an apparatus according to some embodiments. The lens tip 100 includes a lens housing 101 and a first lens 102 that is coupled to an inner surface of the lens housing 101. In some embodiments, the first lens 102 may be concave with a curvature similar to the curvature of an eye. The first lens 102 can be glued into a first end of the lens housing 101, and the glue can provide a seal against moisture intrusion. As shown in FIG. 2, a second lens 204 is coupled to a lens holder 206. Mounting the first lens 102 in the lens housing 101 and the second lens 204 in the lens holder 206 may provide easier handling without smudging or risk of dropping the first lens 102 and the second lens 204.

Referring to FIG. 3, the lens holder 206 can be mounted in the lens housing 101. The lens holder 206 can be held into a second end of the lens housing 101 using an O-ring 310 positioned between the first lens 102 and the lens holder 206 to seal against dust and debris. In addition, pins 308 can be inserted through holes in the lens housing 101 to hold the second lens 204 in the lens housing 101. The purpose of the pins 308 is so that a jig can be used to press the pins 308 out, thus separating the first lens 102 and the second lens 204 for easy replacement or cleaning without having to deal with cleaning or dissolving glue.

FIGS. 4-7 illustrate perspective views of a lens tip 100 according to some embodiments. The lens tip 100 can include magnets 412, or another coupling mechanism (e.g., screws), for coupling the lens tip 100 to an imaging device. One or more sides 414 of the lens tip 100 may be substantially flat so that it is easier for a fixture to access the pins 308 for insertion and removal. In some embodiments, the one or more sides 414 can be concave. In addition, the sides can serve as a way to hold the lens tip 100. There may be a polarization effect on the lenses, and the lenses can be rotated in the lens tip 100 to remove small glints in an image, and the sides can enable the rotation of the lenses.

Figure 6:
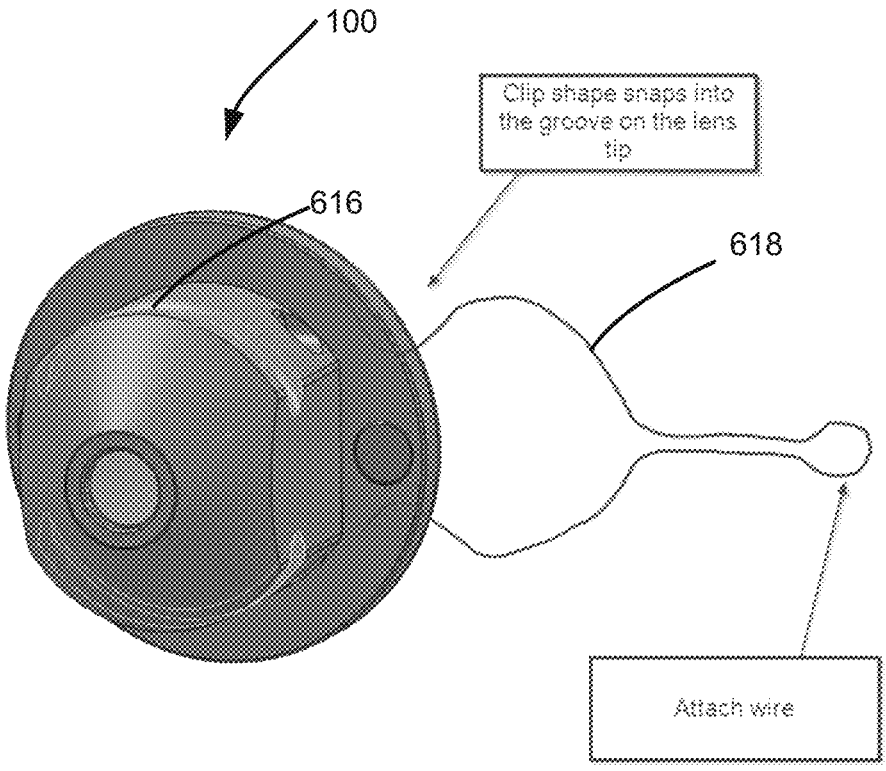
FIG. 6 illustrates another perspective view of a lens tip according to some embodiments.

Referring to FIG. 6, the lens tip 100 may additionally include one or more grooves 616 for holding a wire 618. The wire 618 may connect (e.g., electrically connect) the lens tip 100 to a device. The device to which the lens tip 100 may be connected may be an electroretinogram (ERG) device, in which case the lens tip 100 can be coated in a conductive material, for example, gold plating, to make electrical contact with the cornea of an eye. The grooves 616 can allow the wire 618 to snap into place so that electrically conductive contacts (e.g., electrodes) can be attached to a digital amplifier that monitors for a signal.

Figure 7:
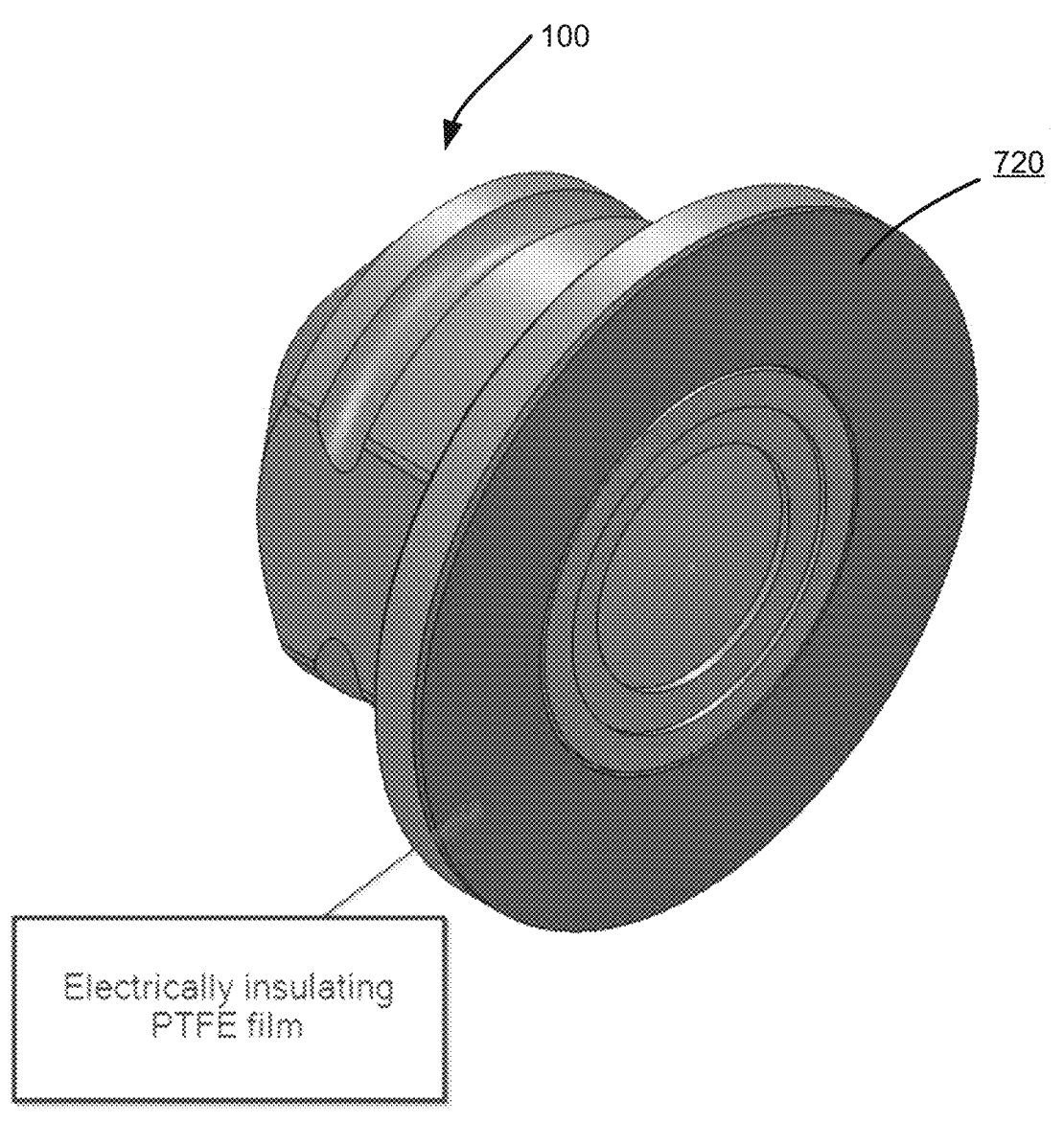
FIG. 7 illustrates another perspective view of a lens tip according to some embodiments.

In FIG. 7, a backside surface 720 of the lens tip 100 can include polytetrafluoroethylene (PTFE) or other electrically insulating material to electrically isolate the lens tip 100 from the rest of the imaging device. As a result, the electrically conductive contacts may not pick up stray signals (e.g., from the imaging device itself or other electrical signals in a vicinity of the imaging device) other than the intended signals from the cornea. In addition, the electrically insulating material can allow the lens tip 100 to easily slide on a magnetic surface of the imaging device.

Figure 8:
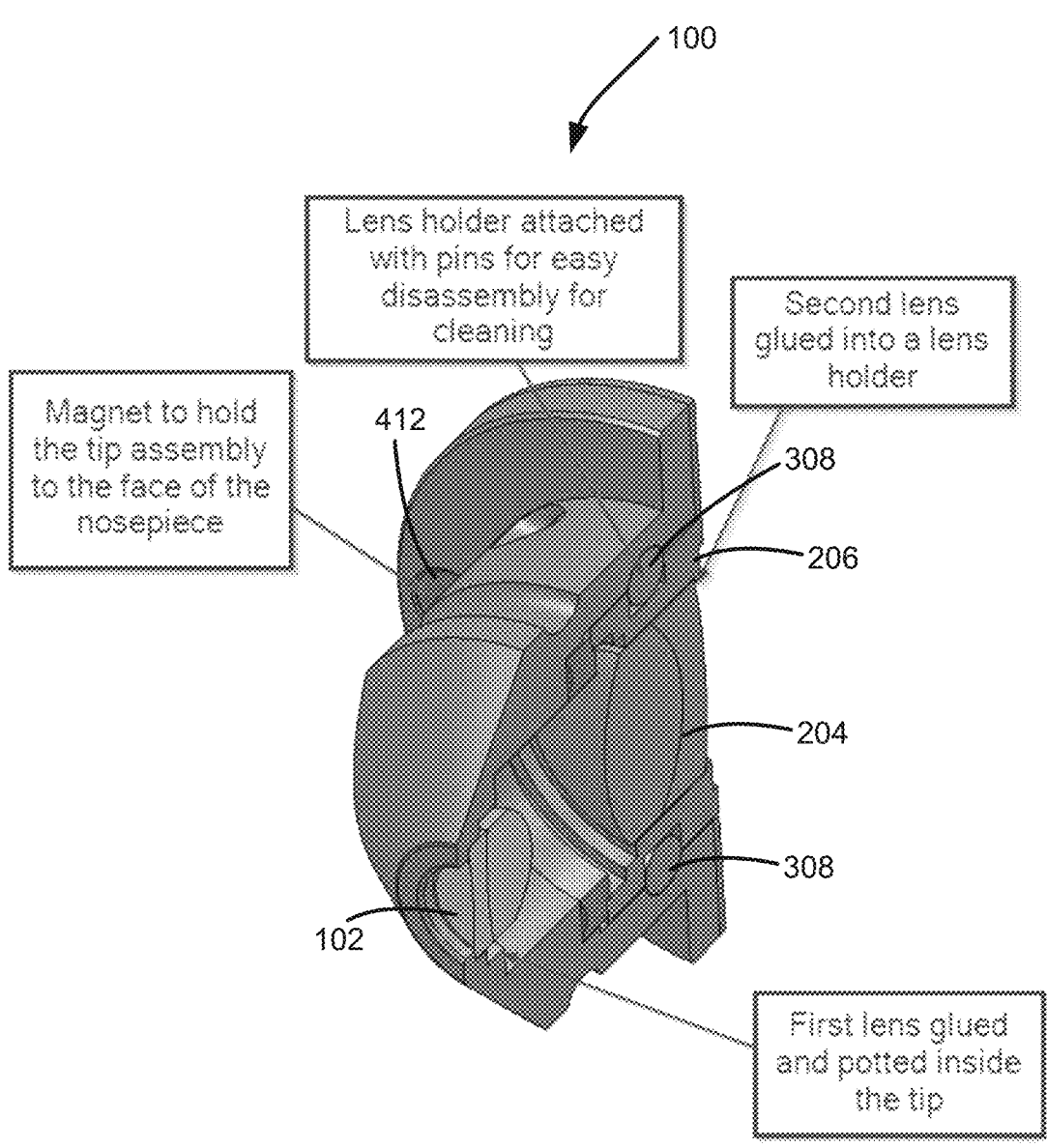
FIG. 8 illustrates a section view of a lens tip according to some embodiments.

FIG. 8 illustrates a section view of a lens tip 100 according to some embodiments. The lens tip 100 includes a first lens 102 glued and potted inside the lens tip 100 and a second lens 204 glued and potted in a lens holder 206 mounted in the lens tip 100. The lens holder 206 is attached to the lens holder 206 with pins 308 for easy disassembly and cleaning. In addition, magnets 412 hold the lens tip 100 to a face of an imaging device.

Figure 9:
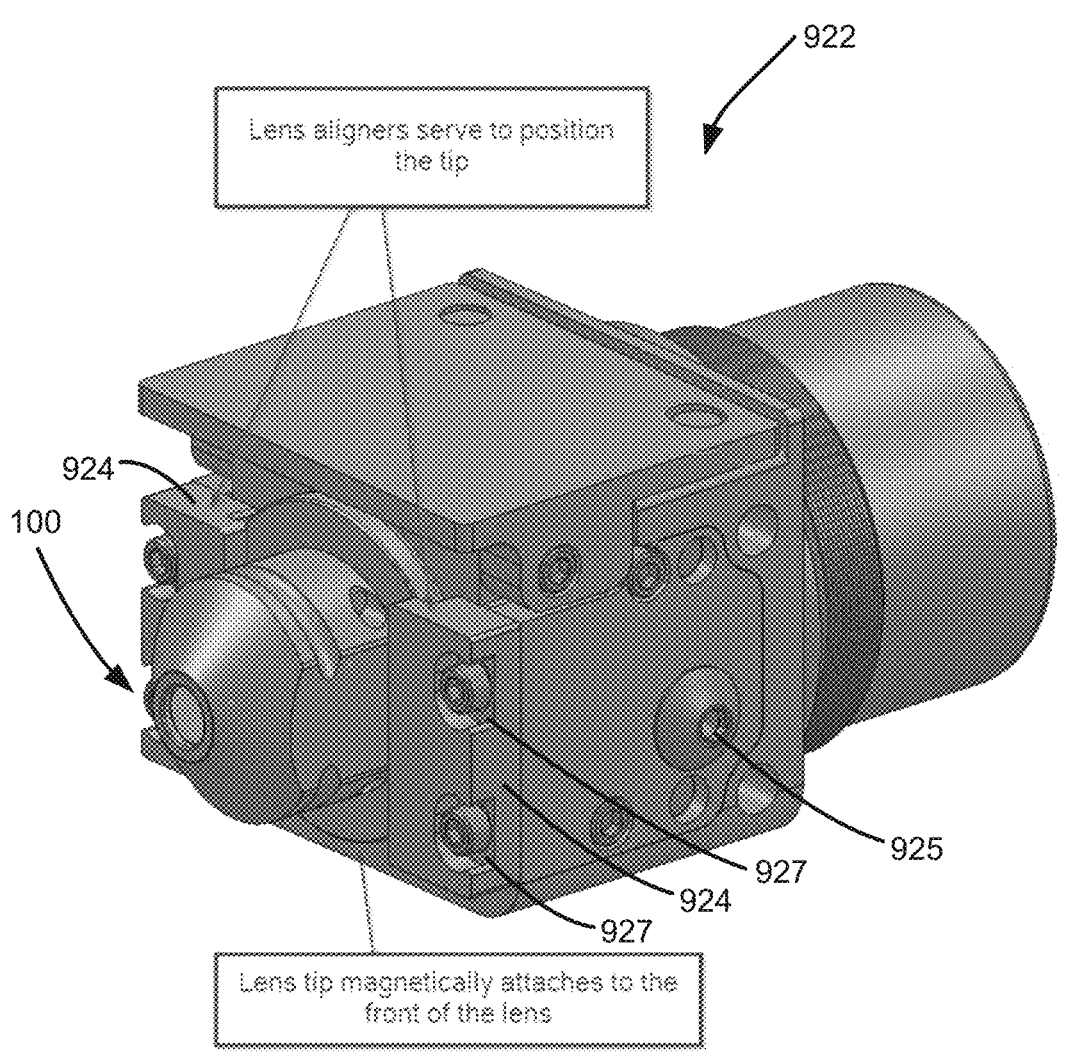
FIG. 9 illustrates a perspective view of a lens assembly of an imaging device according to some embodiments.

FIG. 9 illustrates a perspective view of a lens assembly 922 of an imaging device according to some embodiments. A lens tip 100 is magnetically coupled to a front region of the lens assembly 922. The lens assembly 922 can include lens aligners 924 to position the lens tip 100 with respect to the lens assembly 922. Screws, or another attachment mechanism, can be used to couple the lens aligners 924 to the lens assembly 922. In addition, a screw 925 in a side of the lens assembly 922 can plug a threaded hole. If the screw 925 is removed, a thumb screw can be inserted into the threaded hole for easy handling of the lens aligner 924. The lens aligner 924 also includes slots 927 for positioning the lens aligner 924 as needed.

Figure 10:
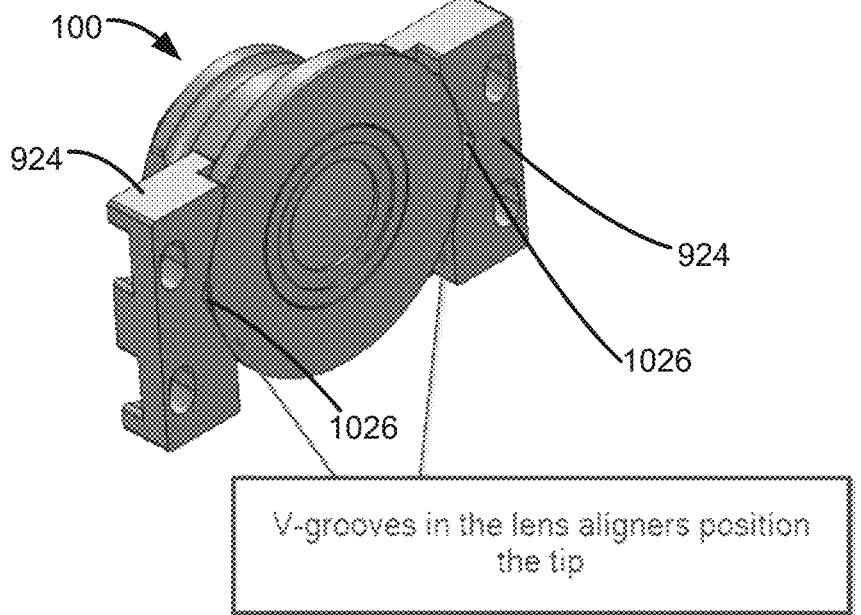
FIG. 10 illustrates a perspective view of lens aligners including one or more v-grooves according to some embodiments.
Figure 11:
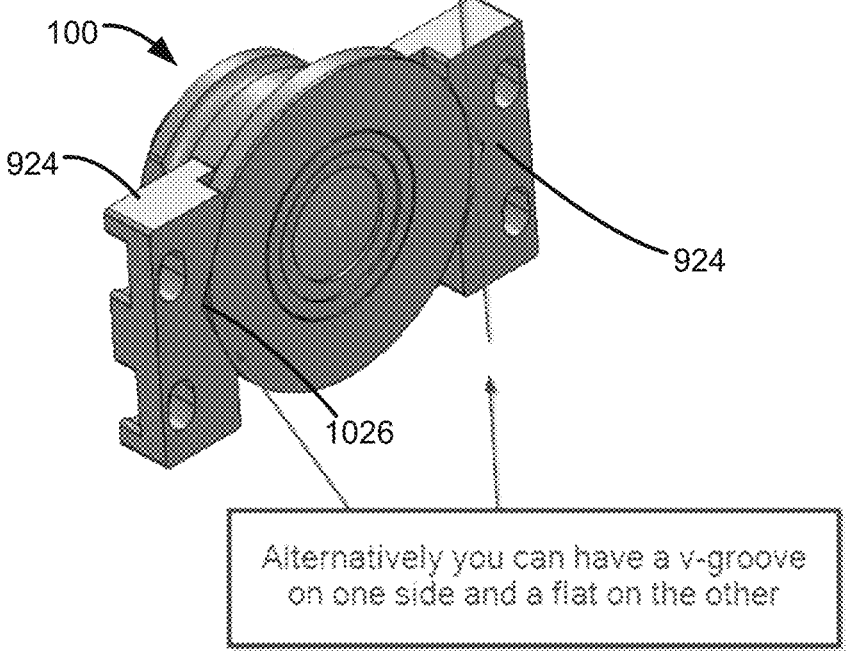
FIG. 11 illustrates a perspective view of lens aligners including one or more v-grooves according to some embodiments.

As shown in FIGS. 10-11, the lens aligners 924 can include one or more v-grooves 1026 to position the lens tip 100 with respect to the lens assembly. In FIG. 10, each of the lens aligners 924 includes a v-groove 1026. Alternatively, in FIG. 11, only one of the lens aligners 924 includes a v-groove 926, while the other lens aligner 924 is flat. The lens assembly can include a dichroic beamsplitter and inserting the dichroic beamsplitter into the lens assembly from the side can cause the lens tip 100 to move up or down depending on the position of the v-groove 1026. With one lens aligner having a v-groove and the other being flat, only one side may need to be adjusted to position the lens tip 100.

Figure 12:
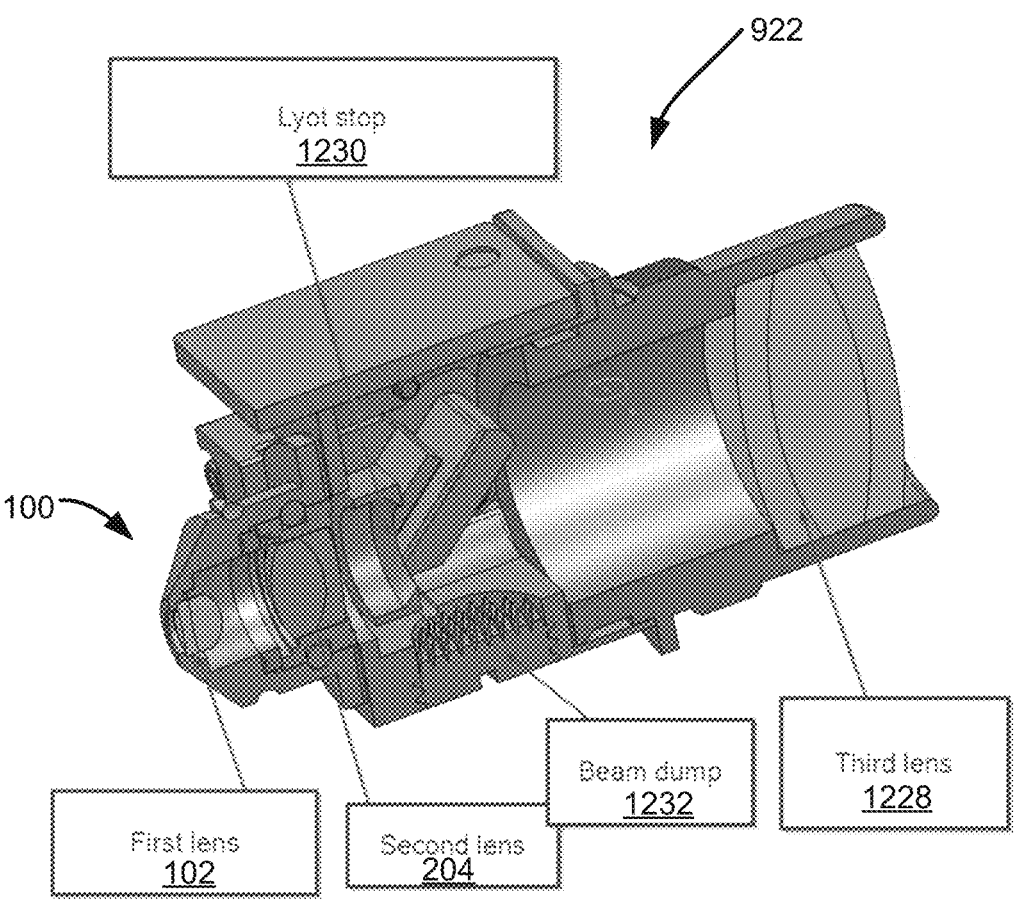
FIG. 12 illustrates a section view of a lens tip and a lens assembly according to some embodiments.

FIG. 12 illustrates a section view of a lens tip 100 and a lens assembly 922 according to some embodiments. In addition to a first lens 102 and a second lens 204 in the lens tip 100, the lens assembly 922 can include a third lens 1228 that may be concentric with the first lens 102 and the second lens 204 so that light from the first lens 102 and the second lens 204 is colinear with an axis of the third lens 1228. The lens assembly 922 can additionally include a Lyot stop 1230 to improve image quality by limiting an amount of light that enters the lens tip 100 and/or the third lens 1228. In some examples, the lens assembly 922 also includes a beam dump 1232 to reduce light reflecting off the dichroic beamsplitter from reflecting back into an image. The beam dump 1232 can be a textured surface coated with a dark (e.g., black) paint.

Figure 13:
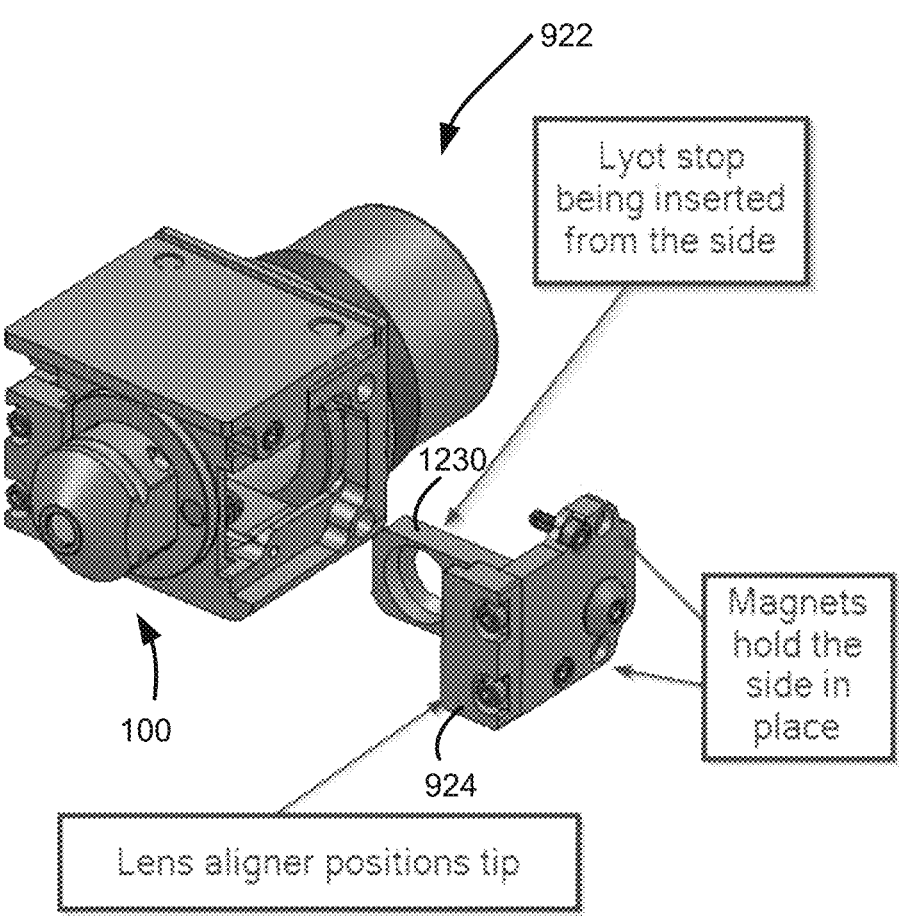
FIG. 13 illustrates another perspective view of a lens assembly according to some embodiments.
Figure 14:
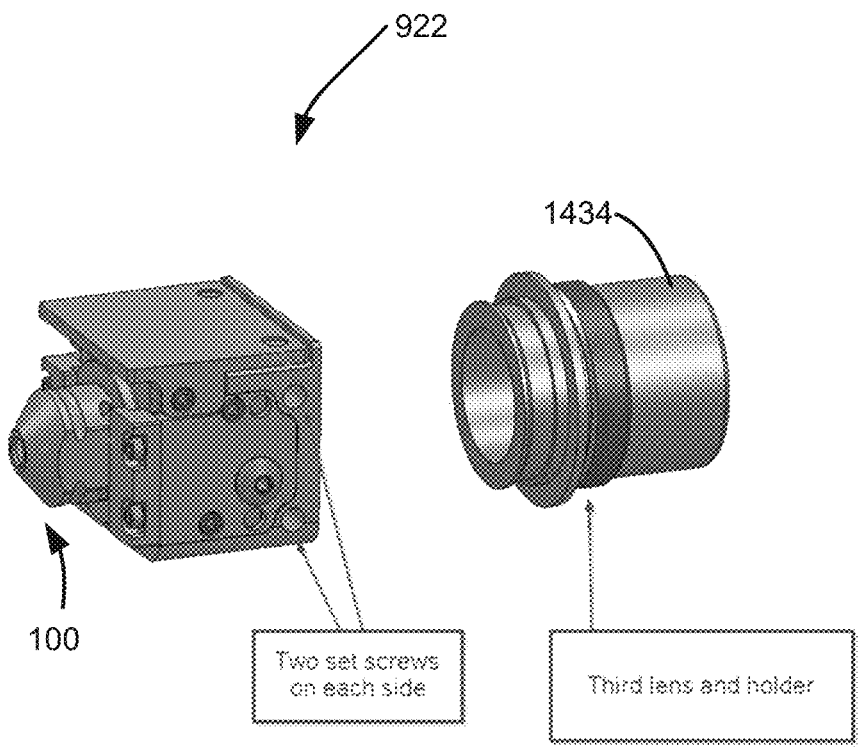
FIG. 14 illustrates another perspective view of a lens assembly according to some embodiments.
Figure 15:
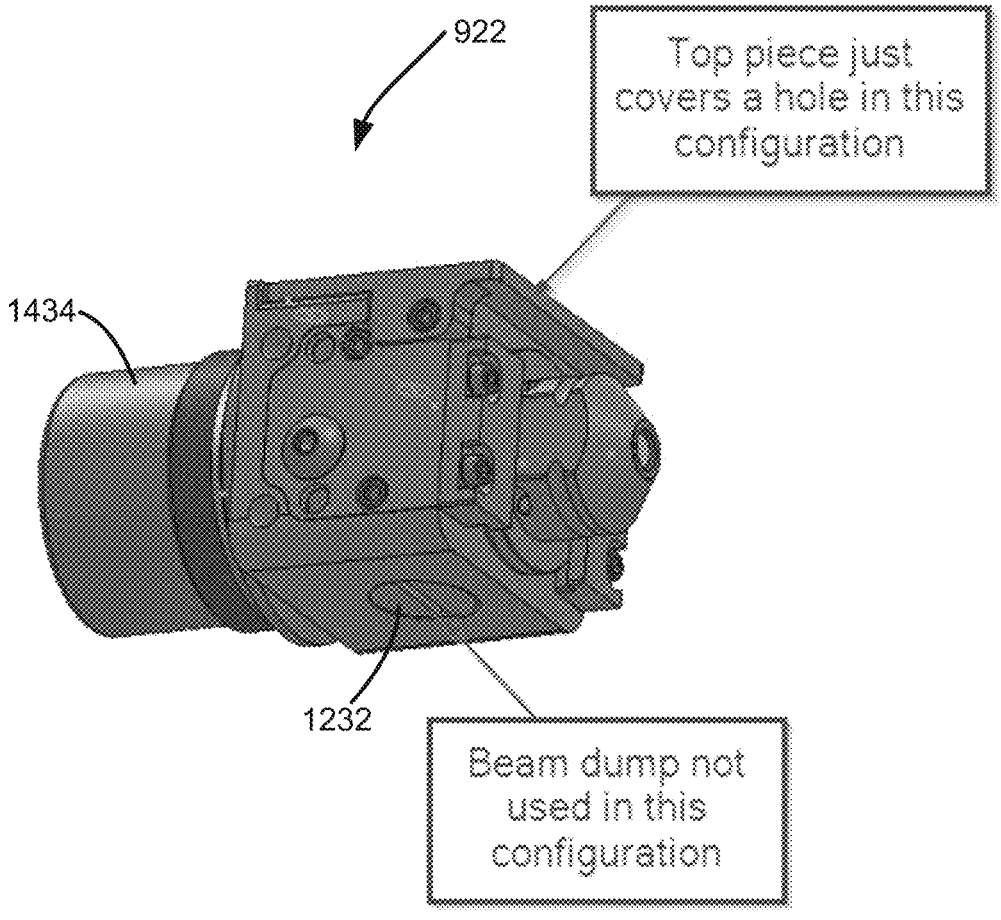
FIG. 15 illustrates another perspective view of a lens assembly according to some embodiments.

FIGS. 13-15 illustrate additional perspective views of a lens assembly 922 according to some embodiments. A side of the lens assembly 922 can be removed to pull out the Lyot stop 1230. When the side piece is inserted, and then held in place with magnets, the lens aligners 924 engage and position the lens tip 100 accordingly. As shown in FIG. 14, a third lens (not shown) is glued into another lens holder 1434. The lens holder 1434 can have threads that attach to a camera. In some examples, the lens holder 1434 can independently rotate the third lens from the rest of the lens assembly 922 because it also has a polarization effect which can introduce image artifacts. As shown in FIG. 15, the lens assembly 922 also includes a beam dump 1232 on a bottom side and a top piece that may serve different functionality depending on the configuration of the imaging device. For example, the top piece of FIG. 15 may cover a hole in a top side of the lens assembly 922.

Figure 16:
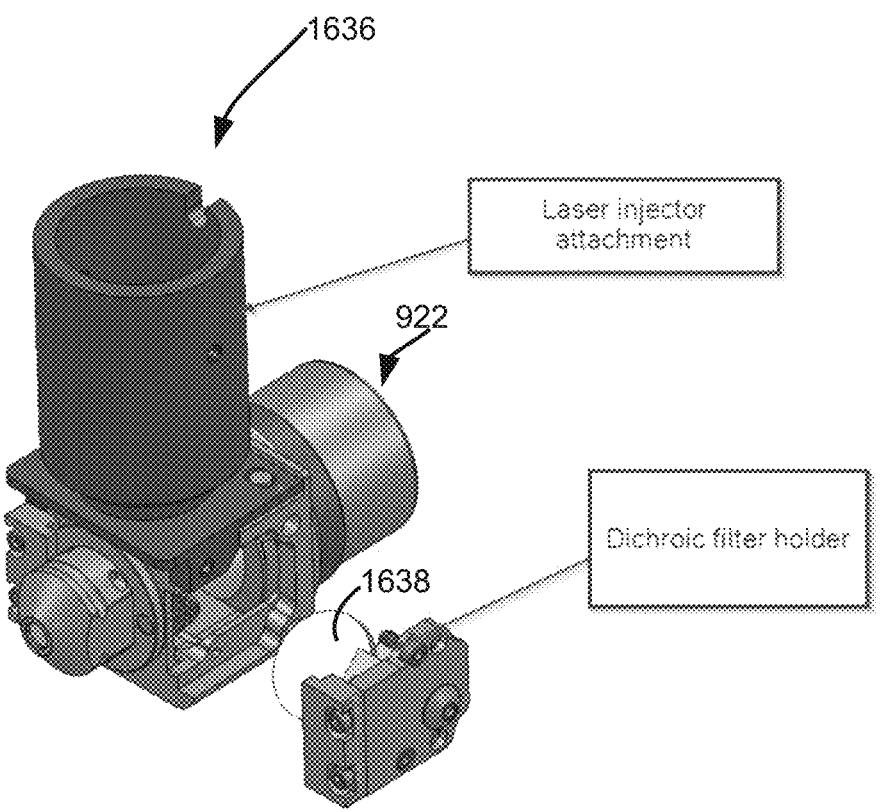
FIG. 16 illustrates views of a laser injector attachment coupled to a lens assembly according to some embodiments.

FIG. 16 illustrates views of a laser injector attachment 1636 coupled to a lens assembly 922 according to some embodiments. In this case, the Lyot stop can be replaced with a dichroic beamsplitter 1638. Replacing the Lyot stop with a filter holder can enable the ability to add attachments to the lens assembly 922. In addition, the top piece can be removed and replaced with a specialized adapter depending on the attachment. The laser injector attachment 1636 can project a laser into the lens assembly 922 during imaging of an eye. Other attachments can include an optical coherence tomography (OCT) device, an ERG device, etc.

Figure 17:
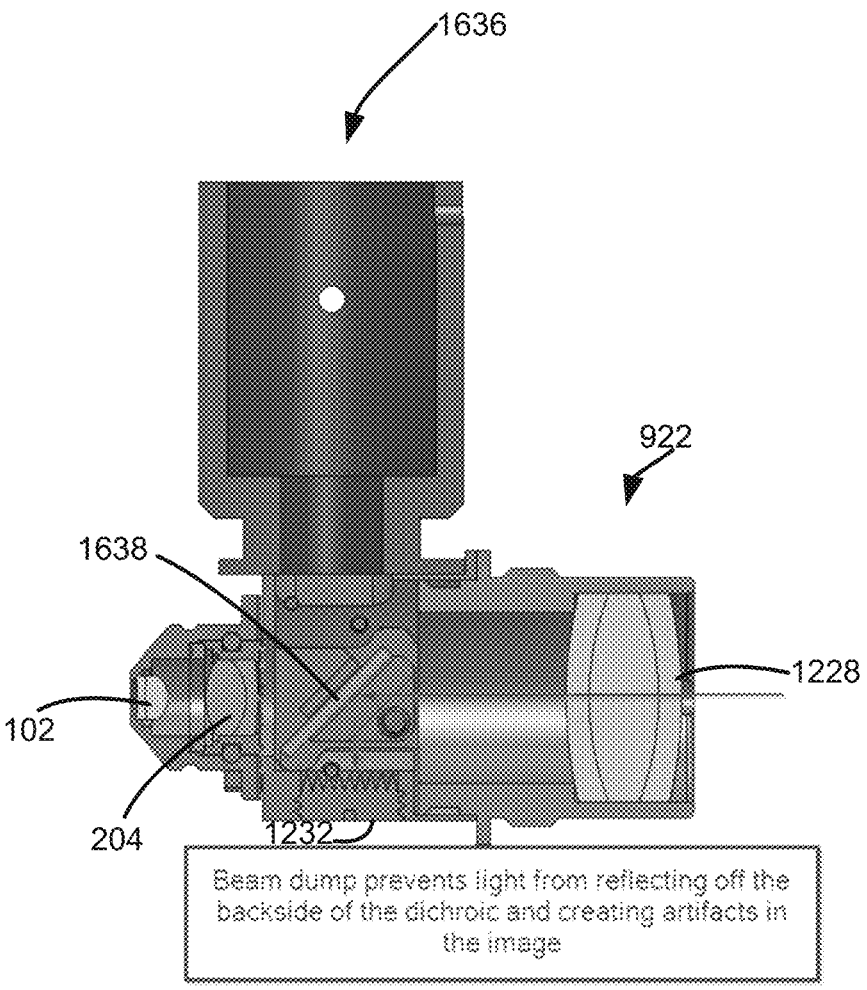
FIG. 17 illustrates a section view of an imaging device with a beam dump according to some embodiments.
Figure 18:
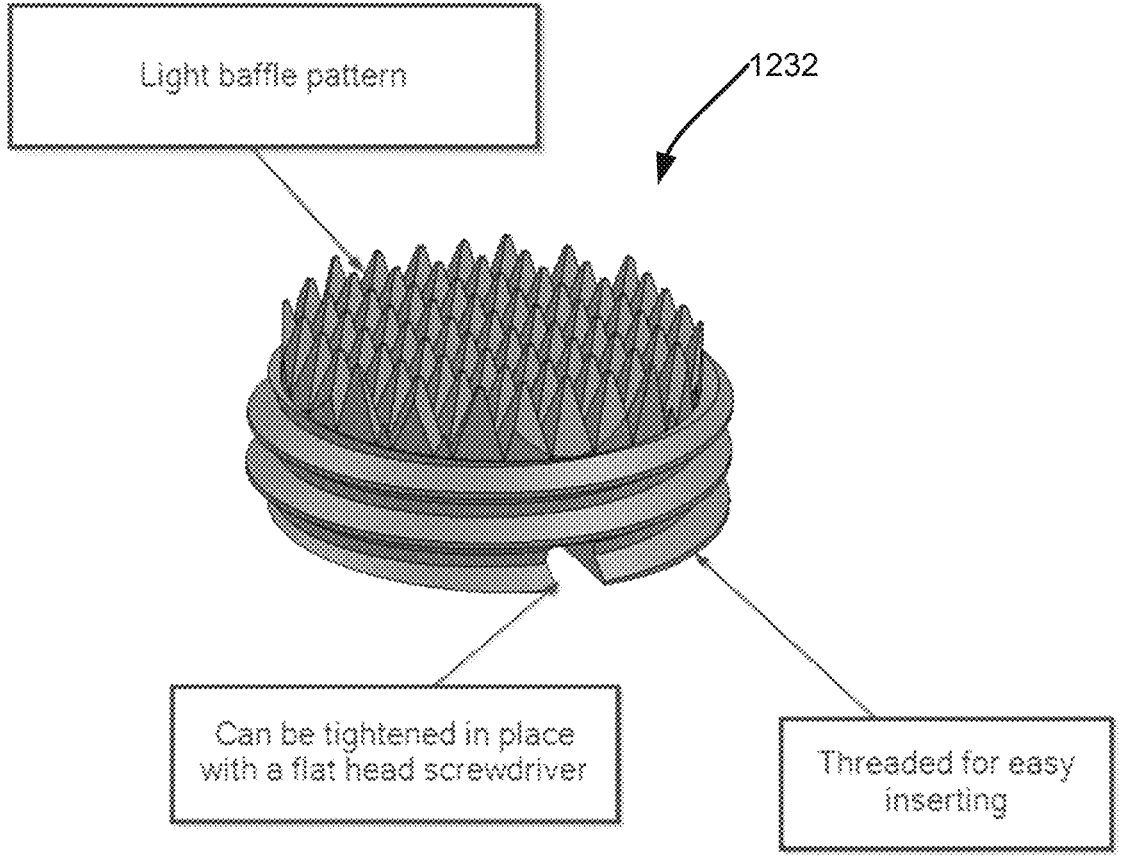
FIG. 18 illustrates a perspective view of a beam dump according to some embodiments.

FIG. 17 illustrates a section view of an imaging device with a beam dump 1232 according to some embodiments. Light can propagate from the laser injector attachment 1636 into the lens assembly 922 for imaging. When a dichroic beamsplitter 1638 is in place, the beam dump 1232 can prevent light from reflecting off the backside of the dichroic beamsplitter 1638, illustrated with the arrow in FIG. 17, from creating artifacts in the image. An exemplary beam dump 1232 is shown in FIG. 18. The beam dump 1232 is an inserted piece with a light baffle on top. The light baffle can be painted with an anti-reflective coating (either black or carbon infused coatings) to prevent any reflections from coming into play in the image. The beam dump 1232 can include threads for coupling the beam dump 1232 to the lens assembly 922.

Figure 19:
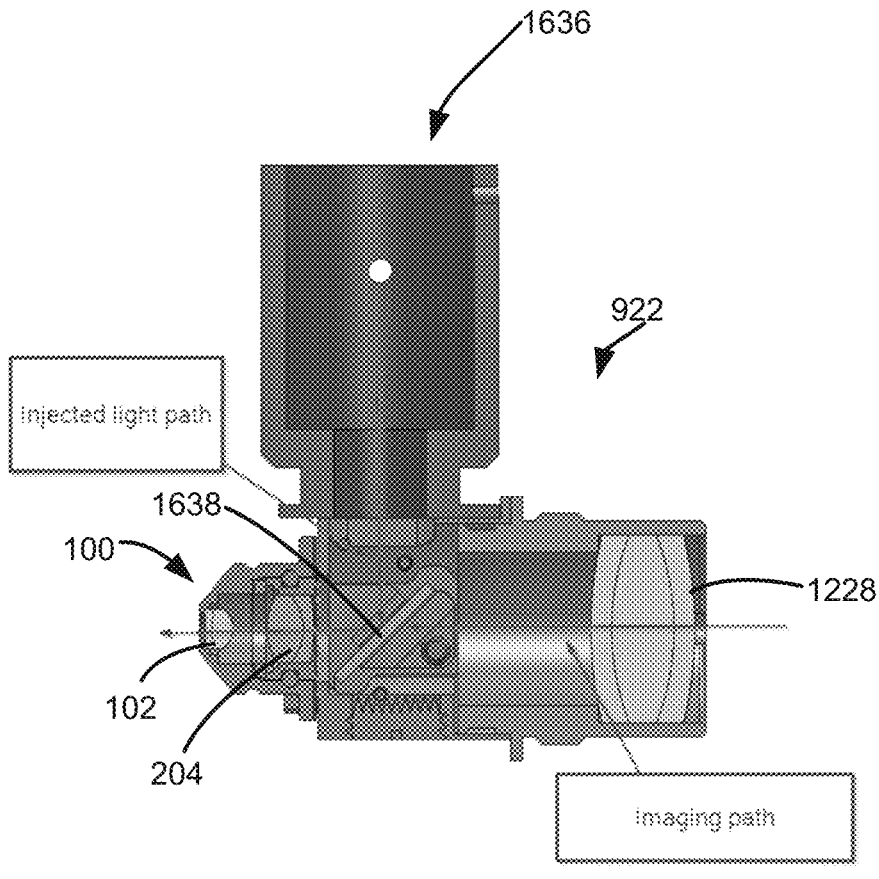
FIG. 19 illustrates a section view of an imaging device and a path of light in the imaging device with a laser injector attachment, a lens assembly, and a lens according to some embodiments.
Figure 20:
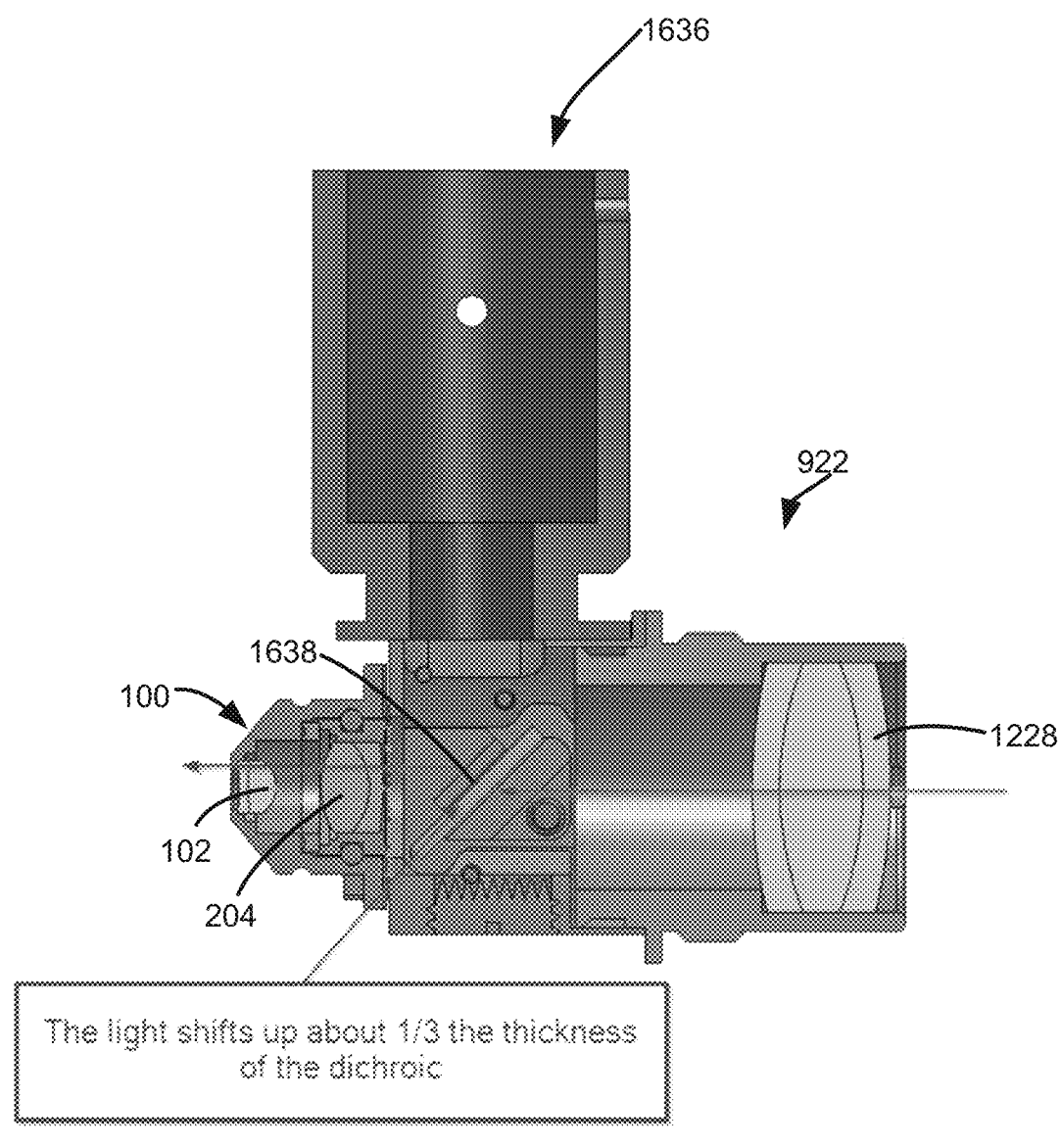
FIG. 20 illustrates another section view of an imaging device and a path of light in the imaging device with a laser injector attachment, a lens assembly, and a lens according to some embodiments.
Figure 21:
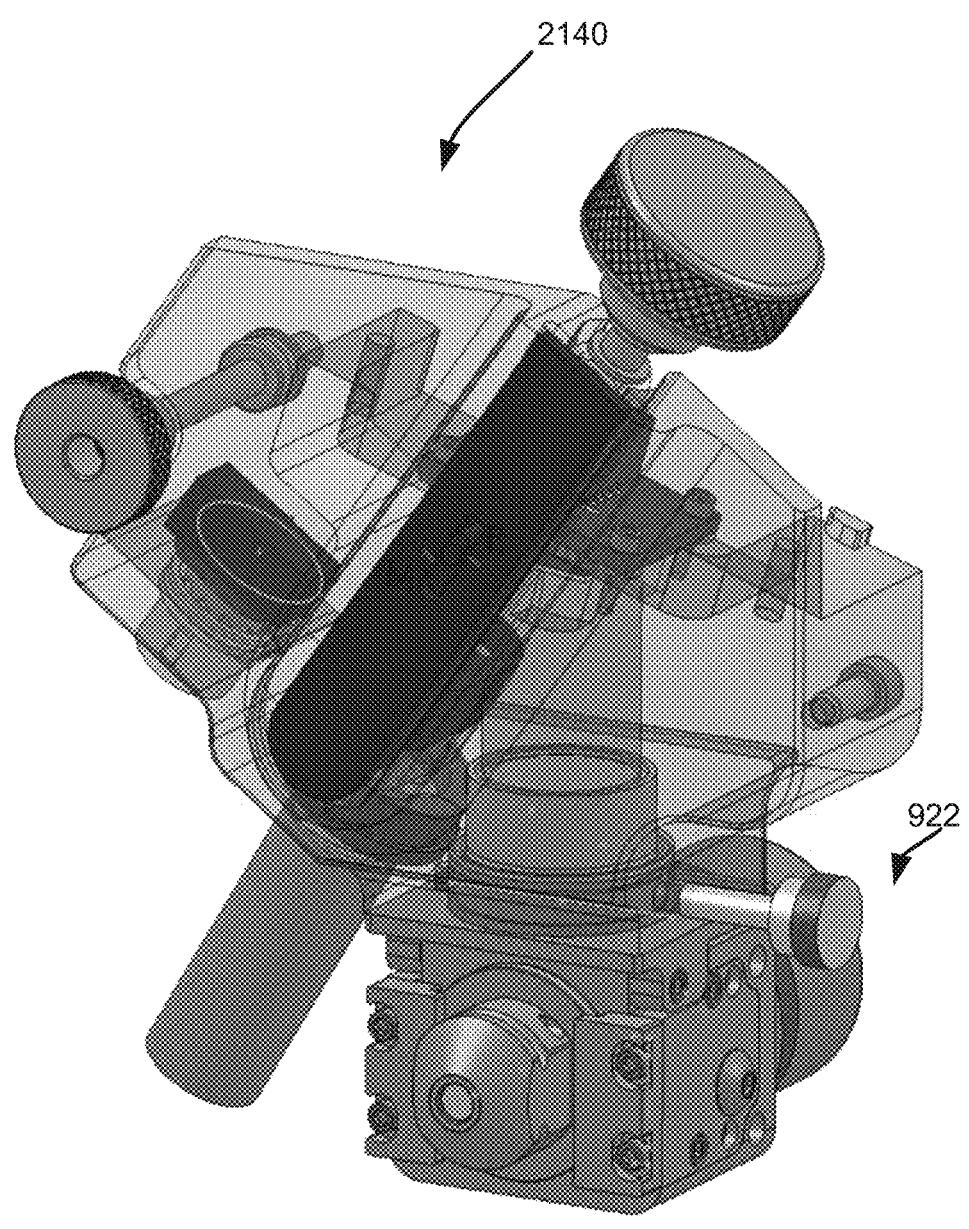
FIG. 21 illustrates a view of an optical coherence tomography device coupled to a lens assembly according to some embodiments.

FIGS. 19-20 illustrate paths of light in an imaging device with a laser injector attachment 1636, a lens assembly 922, and a lens tip 100. As illustrated, light is injected along an injected light path by the laser injector attachment 1636 towards a dichroic beamsplitter 1638 in the lens assembly 922. Light also propagates along an imaging path through a third lens 1228 towards the dichroic beamsplitter 1638. The light is then propagated through and reflected by the dichroic beamsplitter 1638 and is combined while propagating through a second lens 204 and a first lens 102 in the lens tip 100.

The lens aligner (e.g., lens aligner 924 in FIG. 9) can be used in conjunction with the dichroic beamsplitter 1638 in place. The presence of the dichroic beamsplitter 1638 causes the light to shift upwards about one-third of the thickness of the piece of glass in the dichroic beamsplitter 1638 because of the index of refraction. As a result, the first lens 102 and the second lens 204 should also shift up by this amount or they become misaligned and all the masks in the image path are out of place, causing glints and artifacts to show up the image. The v-groove (e.g., v-groove 1026 in FIG. 10) on the lens aligner can provide the alignment of the first lens 102 and the second lens 204 with the third lens 1228 based on the thickness of the dichroic beamsplitter 1638. That is, the act of putting the dichroic beamsplitter 1638 in laterally from the side of the lens assembly 922 forces the lens tip 100 to adjust transversely depending on the position of the v-groove.

As described in FIG. 9, the lens aligner 924 includes slots 927 so that the position of the lens aligner 924 can be adjusted up and down as needed. Therefore, if a first dichroic beamsplitter for a first application (e.g., an OCT scan head) has a first thickness and a second dichroic beamsplitter for a second application (e.g., laser scan head) has a second thickness, the lens aligner 924 and the v-groove can automatically align the lenses for both applications. In some embodiment, a user could remove the first dichroic beamsplitter and insert the second dichroic beamsplitter. The act of inserting the second beamsplitter can reposition the lens tip 100 to where it needs to be for proper alignment, resulting in a fast change between attachments.

Figure 22:
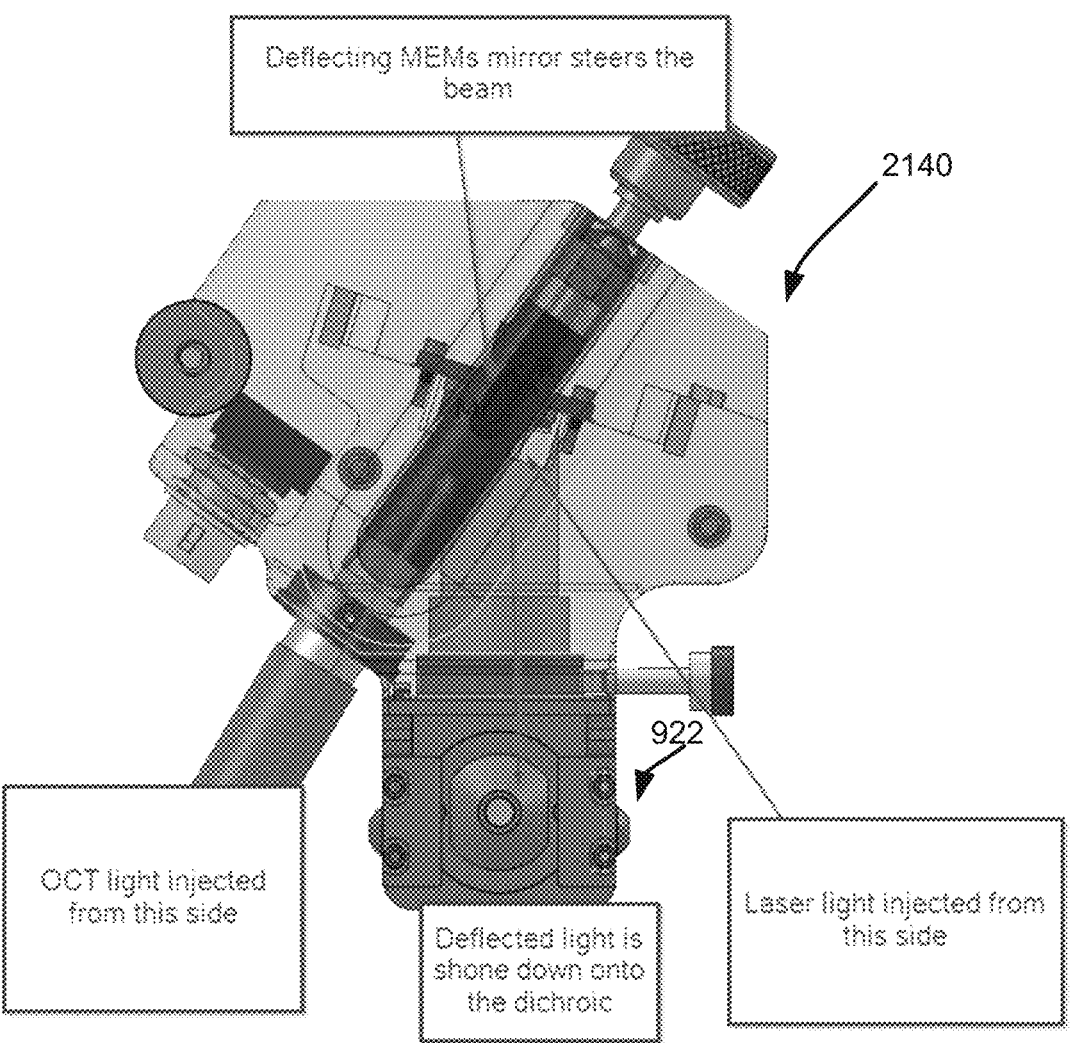
FIG. 22 illustrates a view of an optical coherence tomography device coupled to a lens assembly according to some embodiments.
Figure 23:
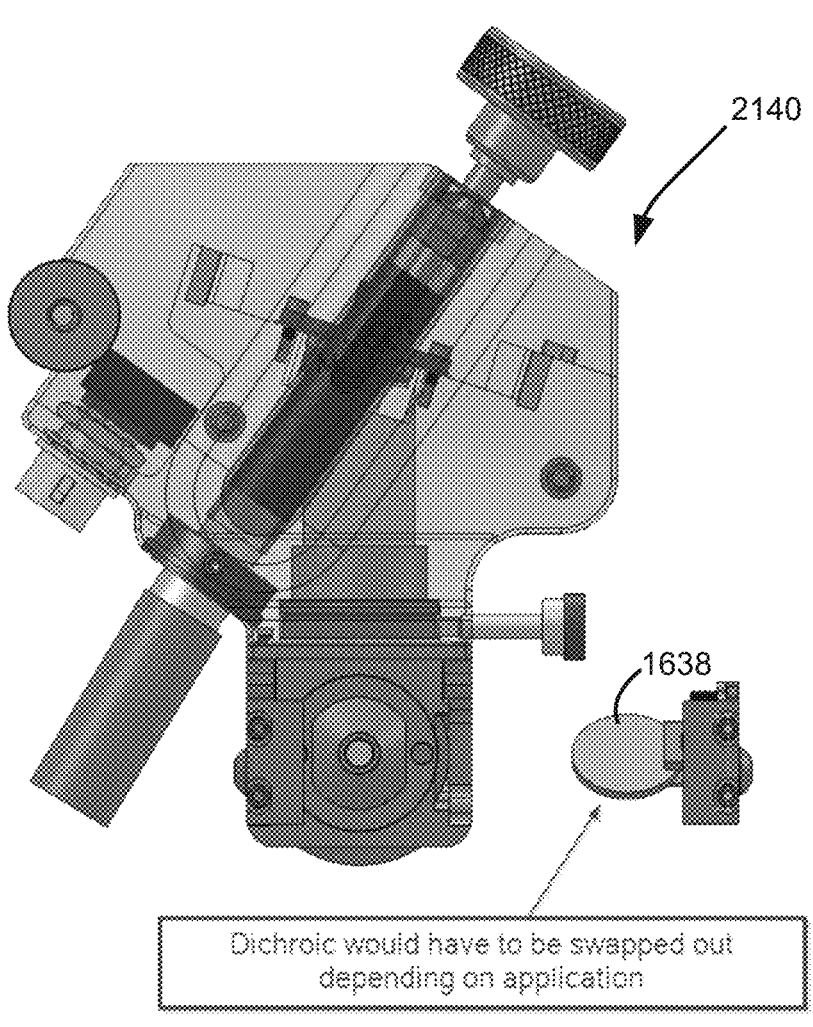
FIG. 23 illustrates a view of an optical coherence tomography device coupled to a lens assembly according to some embodiments.
Figure 24:
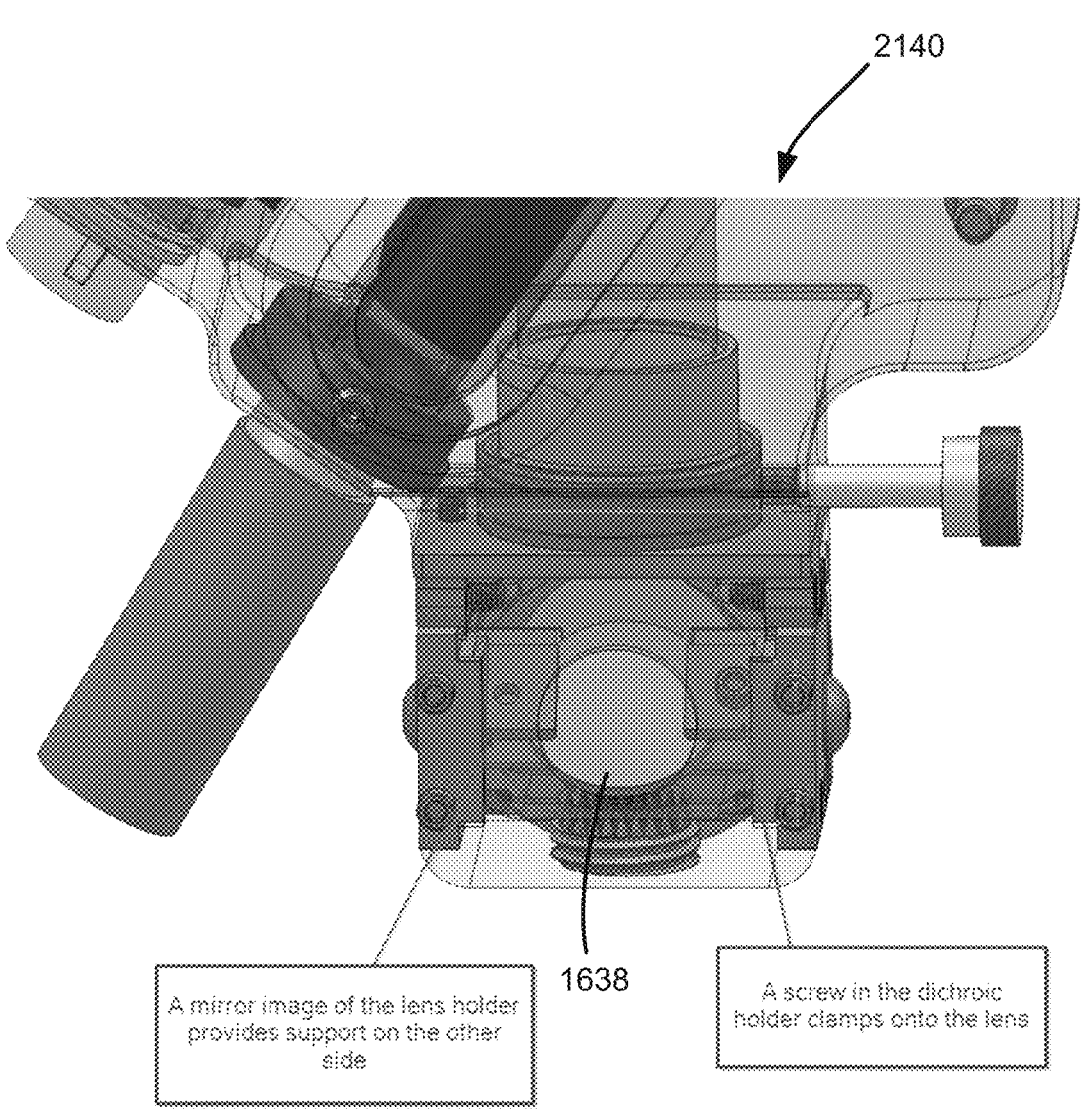
FIG. 24 illustrates a view of an optical coherence tomography device coupled to a lens assembly according to some embodiments.
Figure 25:
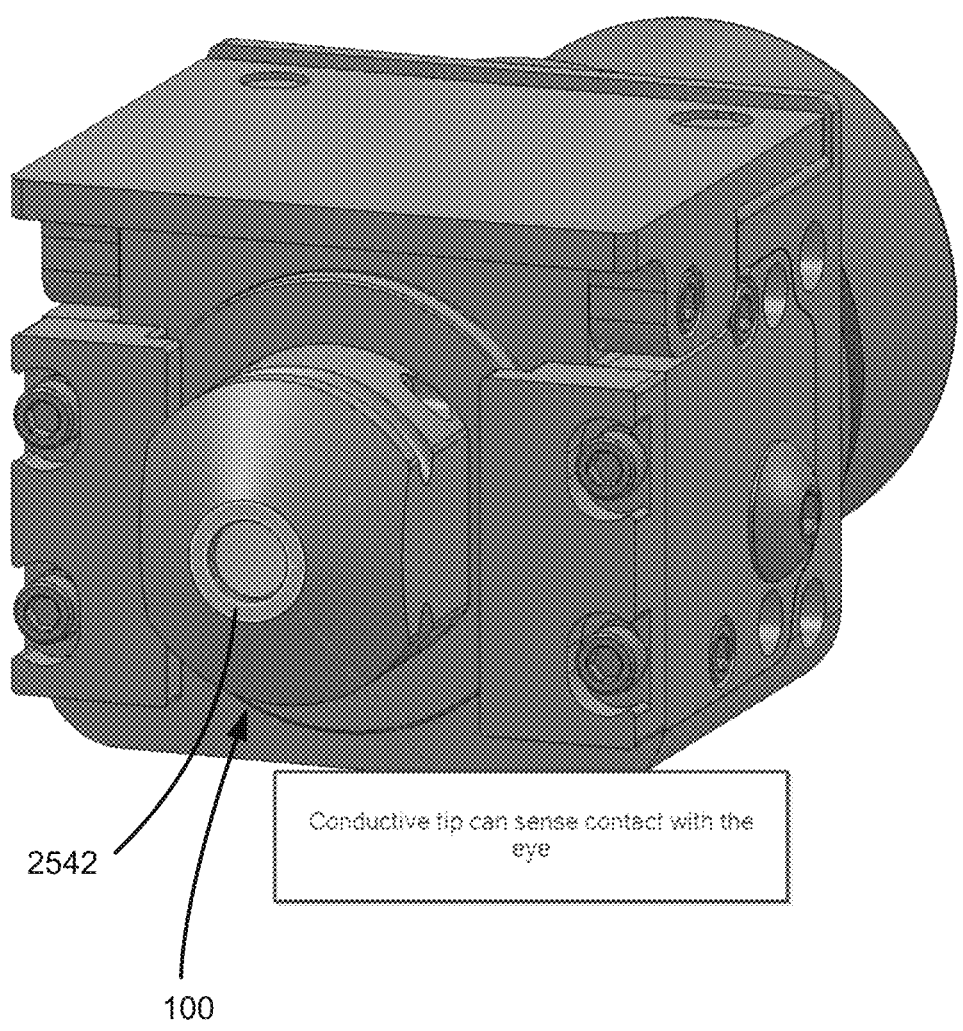
FIG. 25 illustrates a view of a tip of a lens tip according to some embodiments.

FIGS. 21-24 illustrates views of an OCT device 2140 coupled to a lens assembly 922 according to some embodiments. The OCT device 2140 may accommodate OCT light injection or laser light injection into the lens assembly 922. Depending on the light injection, a dichroic beamsplitter of the lens assembly 922 can be changed. As shown in FIG. 22, the OCT device 2140 can include a micro-electro-mechanical systems (MEMS) mirror or another element (e.g., a galvanometer) for steering a light beam. OCT light can be injected from a first side and laser light can be injected from a second side. Light deflected by the MEMS mirror can propagate onto the dichroic beamsplitter 1638 (FIG. 23) in the lens assembly 922. A dichroic holder can be provided on a side of the lens assembly 922 to provide support for the dichroic beamsplitter 1638 such that the dichroic beamsplitter 1638 is not left suspended inside lens assembly 922. By putting a screw in the dichroic holder, it clamps onto the dichroic beamsplitter 1638 and holds it in place.

Figure 26:
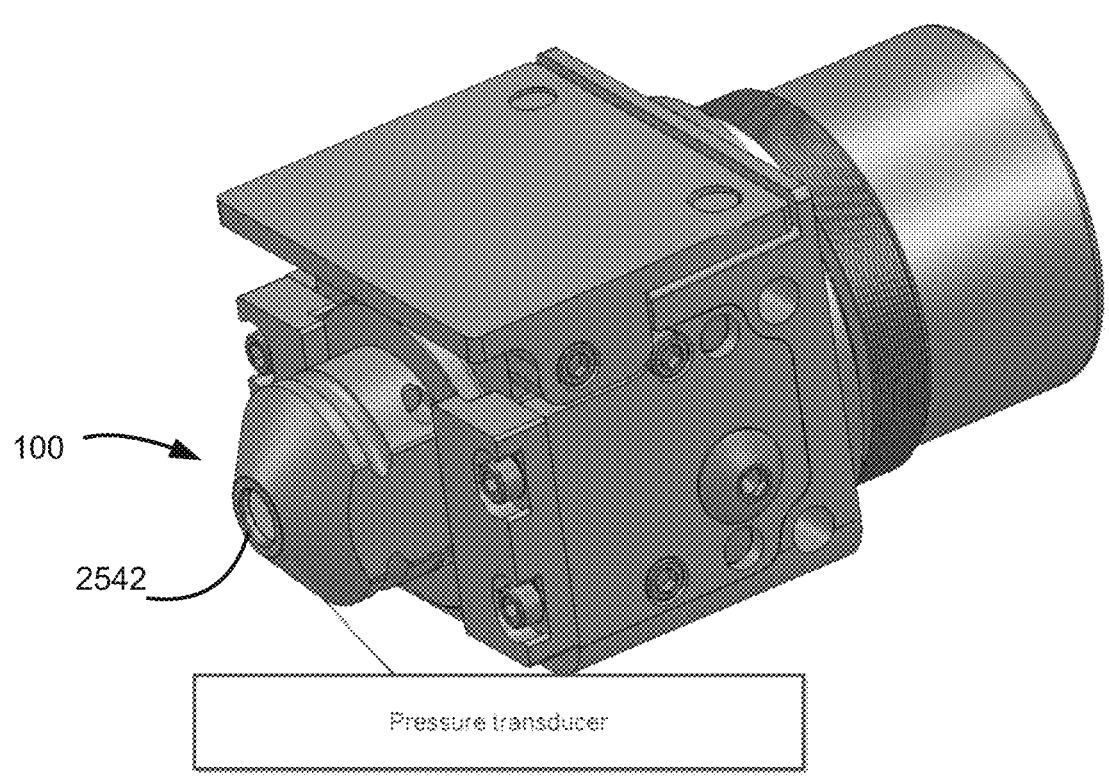
FIG. 26 illustrates a view of a tip of a lens tip according to some embodiments.
Figure 27:
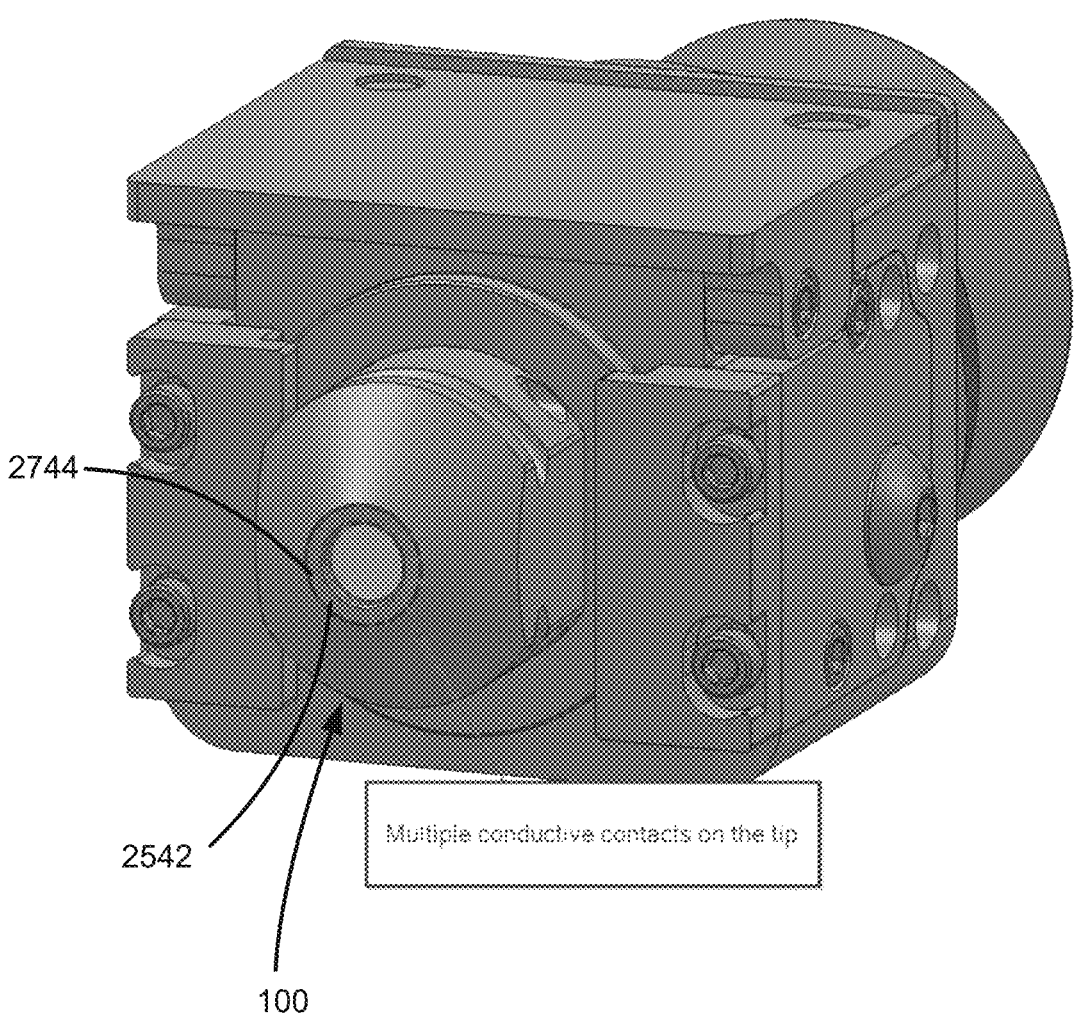
FIG. 27 illustrates a view of a tip of a lens tip according to some embodiments.
Figure 28:
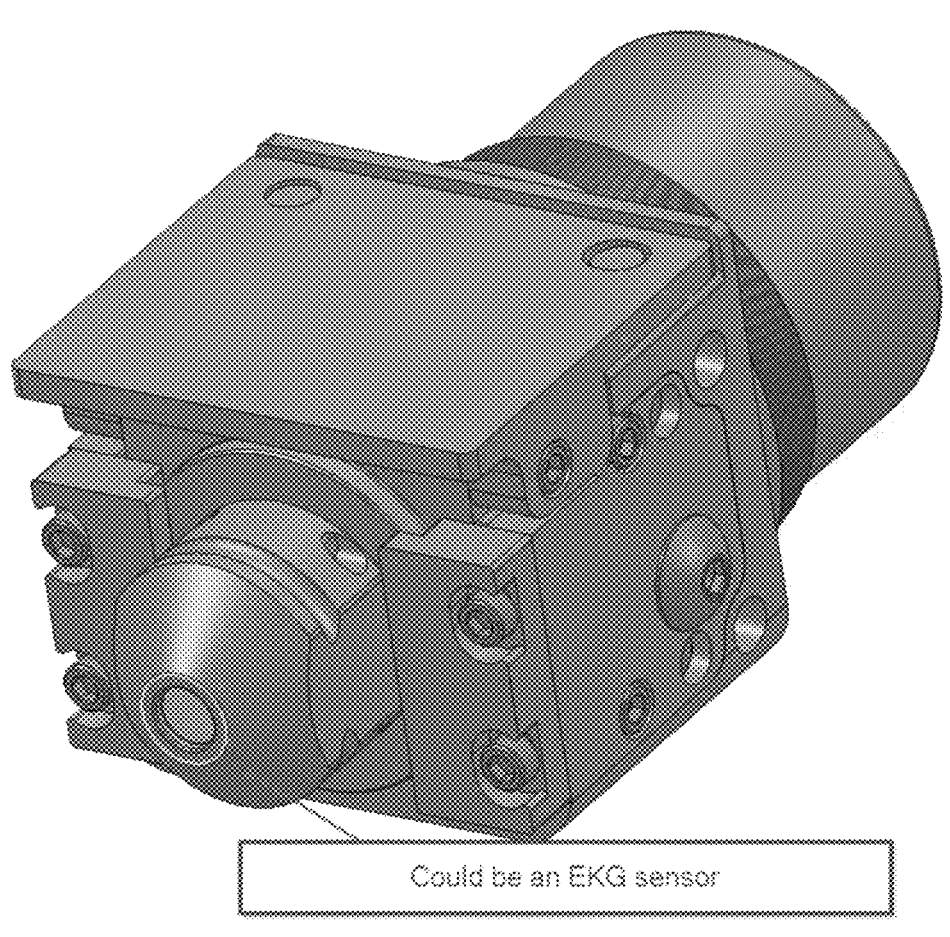
FIG. 28 illustrates a view of a tip of a lens tip according to some embodiments.

FIGS. 25-28 illustrate views of a tip 2542 of a lens tip 100 according to some embodiments. In general, an index matching gel can be used to optically couple the tip 2542 of the lens to the eye. If there is inadequate gel, or an air bubble, this causes a bright spot to appear on the fringes of the image and creates a poor-quality image. Thus, adequate gel should be provided on the lens coupling the lens tip 100 to the eye. If the tip 2542 is conductive and connected to sensing electronics, it can be determined when the tip 2542 has made contact with the eye, which can in turn trigger an auto-focus mechanism. The tip 2542 may be a 3D printed circuit board. The tip 2542 can be conductive so that when the tip 2542 touches the eye sensors in communication with the tip 2542, the imaging device can monitor the eye. The sensor may be an ERG sensor, an electrocardiogram (EKG) sensor (as shown in FIG. 28), a pressure transducer, etc.

As illustrated in FIG. 26, the tip 2542 may be a pressure transducer. The pressure transducer may determine how much force is applied to the eye. Alternatively, the tip 2542 may be floating so that movement is detected. Alternatively, thin filaments can be printed on the tip 2542, and since the resistance of the filaments changes when the filaments deflect, like in a Wheatstone bridge type of load cell, the pressure can be determined based on the deflection. Contacting the eye with the lens tip 100 with too much force may be detrimental to the subject. For instance, if the eye of a baby is contacted with too much force, blood flow to the brain may be reduced, resulting in the baby passing out. The tip 2542 may alternatively be a tonometer that measures an internal pressure of the eye.

As shown in FIG. 27, the tip 2542 may have multiple conductive contacts 2744 that measure a resistance (or lack thereof) between pairs of contacts. Therefore, it can be determined if there is adequate gel contacting the tip 2542 to the eye. The multiple conductive contacts 2744 can also ensure that the tip 2542 is in contact with the whole eye and not off at an angle.

Figure 29:
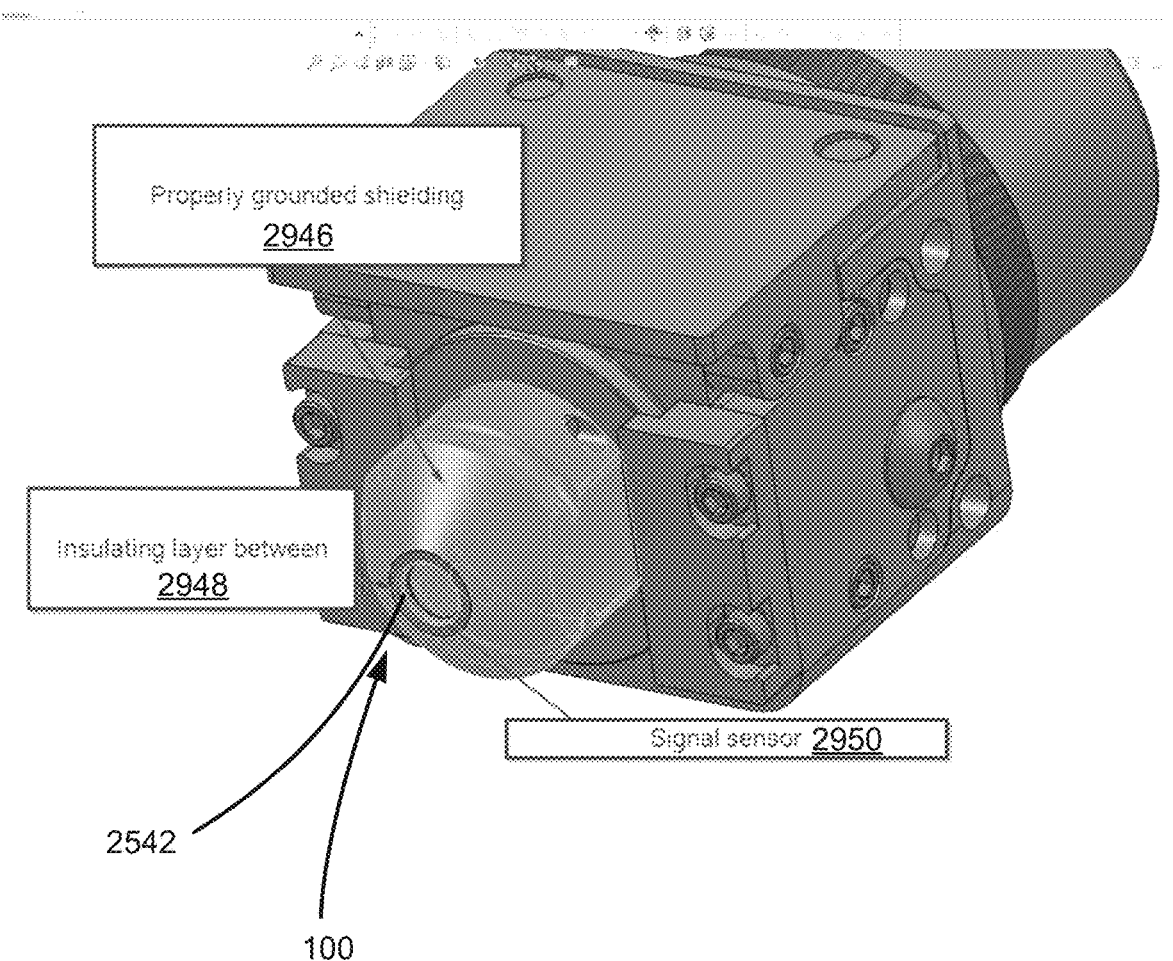
FIG. 29 illustrates a lens tip that is electrically shielded according to some embodiments.
Figure 30:
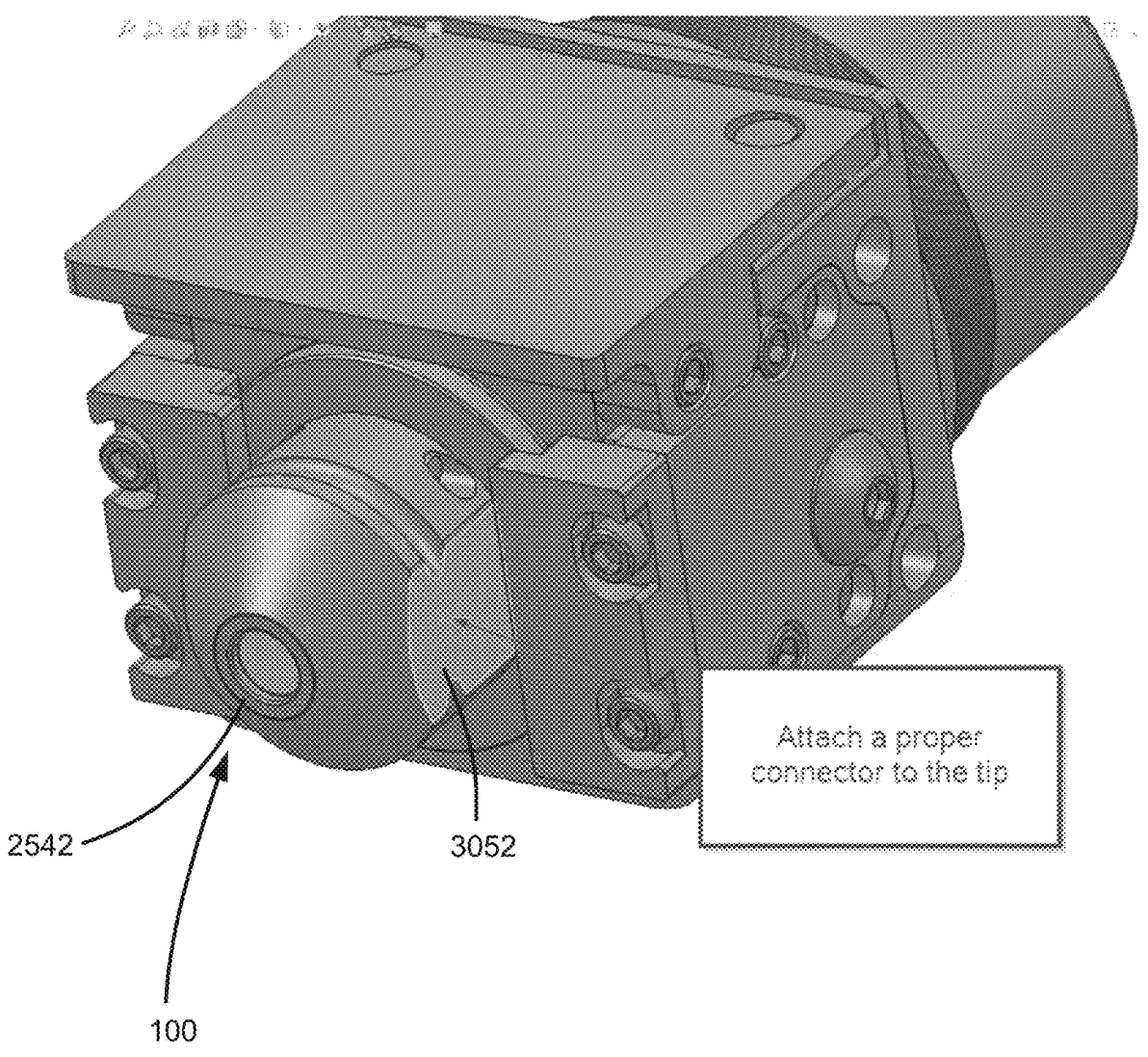
FIG. 30 illustrates a lens tip that is electrically shielded according to some embodiments.

FIGS. 29-30 illustrate a lens tip 100 that is electrically shielded according to some embodiments. A lens tip that is unshielded may act as an antenna and be prone to pick up extraneous noise (e.g., the 60 Hz signal resulting from AC power, movement from a user, or any other signal present in the room). For good signal acquisition, an electrical shielding 2946 that is grounded can be positioned around a sensor 2950 of the tip 2542. The sensor 2950 can be isolated from the shielding 2946 with an insulator 2948 positioned between the sensor 2950 and the shielding 2946. As shown in FIG. 30, the lens tip 100 can be attached to a grounded connector 3052 that is connected to a cable going to electronics. As such, the tip 2542 is shielded against room noise.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. An apparatus comprising:
a lens housing coupled to a lens assembly;
a first lens disposed in a first end of the lens housing;

a lens holder disposed in a second end of the lens housing;
a second lens disposed in the lens holder;
a lens aligner coupled to the lens assembly; and
an optical element insertable laterally into the lens assembly to adjust a transverse position of the first lens and the second lens based on a thickness of the optical element to align a first axis of the first lens and the second lens to a second axis of a third lens positioned in the lens assembly for imaging an eye.

2. The apparatus of claim 1, wherein the optical element comprises a dichroic beamsplitter.

3. The apparatus of claim 1, wherein the optical element comprises a first optical element associated with an optical coherence tomography device, wherein the lens aligner is configured to adjust the transverse position to a first position based on a first thickness of the first optical element, and wherein the apparatus further comprises a second optical element associated with an laser injector attachment, wherein the lens aligner is configured to adjust the transverse position to a second position based on a second thickness of the second optical element.

4. The apparatus of claim 1, wherein the lens aligner comprises one or more v-grooves for adjusting the transverse position of the first lens and the second lens.

5. The apparatus of claim 1, further comprising a tip configured to contact the eye, wherein the tip is electrically conductive.

6. The apparatus of claim 5, wherein the tip comprises a plurality of electrically conductive contacts.

7. The apparatus of claim 5, wherein the tip comprises a pressure transducer.

8. The apparatus of claim 5, wherein the tip comprises an electroretinogram sensor.

9. The apparatus of claim 5, wherein the tip is electrically insulated from the lens assembly.

10. A lens tip of an eye-imaging device, the lens tip comprising:
a lens housing comprising a first lens and a second lens aligned along an optical axis, wherein the lens housing is coupled to a lens assembly and is configured to be positioned with respect to a thickness of an optical element in the lens assembly; and
a tip configured to contact an eye, wherein the tip is electrically conductive;
wherein an optical element is configured to be insertable laterally into the lens assembly to adjust a transverse position of the first lens and the second lens based on the thickness of the optical element to align a first axis of the first lens and the second lens to a second axis of a third lens positioned in the lens assembly for imaging an eye.

11. The lens tip of claim 10, wherein the tip comprises a plurality of electrically conductive contacts.

12. The lens tip of claim 10, wherein the tip comprises a pressure transducer.

13. The lens tip of claim 10, wherein the tip comprises an electroretinogram sensor.

14. The lens tip of claim 10, wherein the tip is electrically insulated from the lens assembly.

* * * * *